United States Patent
Sturm

(10) Patent No.: US 12,394,074 B2
(45) Date of Patent: Aug. 19, 2025

(54) COMPUTED TOMOGRAPHY-BASED PATHWAY FOR CO-REGISTRATION OF INTRAVASCULAR DATA AND BLOOD VESSEL METRICS WITH COMPUTED TOMOGRAPHY-BASED THREE-DIMENSIONAL MODEL

(71) Applicant: PHILIPS IMAGE GUIDED THERAPY CORPORATION, San Diego, CA (US)

(72) Inventor: Bernhard Sturm, Davis, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 196 days.

(21) Appl. No.: 18/028,085

(22) PCT Filed: Sep. 23, 2021

(86) PCT No.: PCT/EP2021/076136
§ 371 (c)(1),
(2) Date: Mar. 23, 2023

(87) PCT Pub. No.: WO2022/069327
PCT Pub. Date: Apr. 7, 2022

(65) Prior Publication Data
US 2023/0334677 A1    Oct. 19, 2023

Related U.S. Application Data

(60) Provisional application No. 63/084,607, filed on Sep. 29, 2020.

(51) Int. Cl.
G06T 7/30    (2017.01)
A61B 5/00    (2006.01)
(Continued)

(52) U.S. Cl.
CPC .............. *G06T 7/30* (2017.01); *A61B 5/7425* (2013.01); *A61B 5/743* (2013.01); *A61B 8/4416* (2013.01);
(Continued)

(58) Field of Classification Search
None
See application file for complete search history.

(56) References Cited

U.S. PATENT DOCUMENTS 7,930,014 B2    4/2011    Huennekens
8,290,228 B2    10/2012    Cohen
(Continued)

OTHER PUBLICATIONS

International Search Report and Written Opinion of PCT/EP2021/076136, dated Apr. 12, 2022.
(Continued)

*Primary Examiner* — Michael J Cobb

(57) ABSTRACT

A co-registration system includes a processor circuit that receives x-ray fluoroscopy images of a blood vessel while an intravascular catheter moves through the blood vessel. The processor circuit also receives intravascular data from the intravascular catheter as the catheter moves through the blood vessel. The processor circuit generates a 2D pathway based on the fluoroscopy images. The processor circuit generates an additional 2D pathway from a 3D CT model. The processor circuit performs a co-registration between the intravascular data and the CT-based 2D pathway based on a mapping between corresponding locations of the fluoroscopy-based 2D pathway and the CT-based 2D pathway. The processor circuit performs an additional co-registration between the intravascular data and the 3D CT model based on the first co-registration and outputs the 3D model with a graphical representation of the intravascular data to a display.

10 Claims, 20 Drawing Sheets

(51) Int. Cl.
*A61B 8/00* (2006.01)
*G06T 7/00* (2017.01)
*G06T 15/00* (2011.01)
*G06T 17/00* (2006.01)

(52) U.S. Cl.
CPC ............ G06T 7/0012 (2013.01); G06T 15/00 (2013.01); G06T 17/00 (2013.01); *G06T 2207/10081* (2013.01); *G06T 2207/10121* (2013.01); *G06T 2207/30021* (2013.01); *G06T 2207/30104* (2013.01)

(56) References Cited

U.S. PATENT DOCUMENTS

| | | |
|---|---|---|
| 8,463,007 B2 | 6/2013 | Steinberg |
| 8,670,603 B2 | 3/2014 | Tolkowsky |
| 8,693,756 B2 | 4/2014 | Tolkowsky |
| 8,781,193 B2 | 7/2014 | Steinberg |
| 8,855,744 B2 | 10/2014 | Tolkowsky |
| 10,076,301 B2 | 9/2018 | Millett |
| 2013/0195338 A1* | 8/2013 | Xu ............... G06T 7/33 382/131 |
| 2014/0254900 A1* | 9/2014 | Sturm ............ A61B 5/489 382/128 |
| 2014/0276085 A1* | 9/2014 | Miller ........... A61B 5/0066 600/467 |
| 2015/0196260 A1 | 7/2015 | Lee |
| 2015/0320325 A1 | 11/2015 | Sheehan |
| 2017/0270705 A1* | 9/2017 | Hopfgartner ..... A61B 6/5211 |
| 2018/0040147 A1* | 2/2018 | Alhrishy ........ A61B 6/5205 |
| 2018/0271614 A1* | 9/2018 | Kunio ........... A61B 90/37 |
| 2021/0077037 A1* | 3/2021 | Kunio ........... G06T 7/70 |
| 2022/0359063 A1* | 11/2022 | Tombropoulos .... G06T 7/0012 |

OTHER PUBLICATIONS

Zhou, Chuan et al, "Automated Coronary Artery Tree Extraction in Coronary CT Angiography using a Multiscale Enhancement and Dynamic Balloon Tracking (MSCAR-DBT) Method", Computerized Medical Imaging and Graphics, vol. 36, No. 1, pp. 1-10, Jan. 2012.

* cited by examiner

COMPUTED TOMOGRAPHY-BASED PATHWAY FOR CO-REGISTRATION OF INTRAVASCULAR DATA AND BLOOD VESSEL METRICS WITH COMPUTED TOMOGRAPHY-BASED THREE-DIMENSIONAL MODEL

TECHNICAL FIELD

The present disclosure relates generally to co-registering data from different medical diagnostic modalities. In particular, intravascular data and blood vessel metrics from angiography images may be co-registered to a three-dimensional computed tomography-based model by co-registering the intravascular data with a computed tomography-based two-dimensional pathway and projecting the intravascular data to the three-dimensional computed tomography-based model.

BACKGROUND

Physicians use many different medical diagnostic systems and tools to monitor a patient's health and diagnose and treat medical conditions. Different modalities of medical diagnostic systems may provide a physician with different images, models, and/or data relating to internal structures within a patient. These modalities include invasive devices and systems, such as intravascular systems, and non-invasive devices and systems, such as x-ray systems, and computed tomography (CT) systems. Using multiple diagnostic systems to examine a patient's anatomy provides a physician with added insight into the condition of the patient.

In the field of intravascular imaging and physiology measurement, co-registration of data from invasive devices (e.g. intravascular ultrasound (IVUS) devices or instantaneous wave-free ratio (iFR) devices) with images collected non-invasively (e.g. via x-ray angiography) is a powerful technique for improving the efficiency and accuracy of vascular catheterization procedures. Co-registration identifies the locations of intravascular data measurements along a blood vessel by mapping the data to an angiography image of the vessel. A physician may then know exactly where in the vessel a measurement was made, rather than estimate the location.

Currently, no method of co-registering intravascular data with a three-dimensional CT model is commercially available. There is also currently no method of co-registering data from an x-ray angiography image (e.g. QCA) with a three-dimensional CT model. If a physician obtains intravascular data or x-ray angiography data of a patient's anatomy as well as a three-dimensional CT model, the physician must estimate the locations of intravascular and angiography data within the CT model which may lead to decreased accuracy in treatment recommendations or procedures.

SUMMARY

Embodiments of the present disclosure are systems, devices, and methods for co-registering intravascular data and angiography data such as blood vessel metrics to a three-dimensional CT-based model. This advantageously provides guidance to the physician concerning locations of features of interest, such as occlusions, within a blood vessel. It also provides exact locations of measurements, such as vessel or lumen diameter, pressure ratio, and blood flow, in a three-dimensional CT-based model giving the physician more accurate and more detailed views of a patient's anatomy. A system configured to perform the co-registration may include an intravascular device, an x-ray imaging device, and a CT device, all in communication with a co-registration system.

In one aspect, the co-registration system receives x-ray fluoroscopy images of a patient vasculature at a given angle while an intravascular device moves through the vasculature collecting data. The intravascular data is mapped to the fluoroscopy images associating the intravascular data with locations along a two-dimensional pathway. The system also receives CT imaging data of the same vasculature which is used to construct a three-dimensional model. The three-dimensional CT-based model is used to create multiple CT-based two-dimensional pathways at different angles. The multiple CT-based pathways are compared to the fluoroscopy-based pathway. The system identifies the CT-based pathway that is most similar to the fluoroscopy-based pathway. The locations along the fluoroscopy-based pathway are mapped to the same locations along the selected CT-based pathway and the intravascular data is associated with corresponding locations of the CT-based pathway. The two-dimensional CT-based pathway and its associated intravascular data is then projected back to the three-dimensional CT-based model. The intravascular data may then be displayed at the correct locations within the three-dimensional CT-based model.

In another aspect, the system may receive an angiography image at any angle and calculate angiography-based data using the image (e.g. QCA data). The angiography-based data may similarly be mapped to corresponding locations along a CT-based two-dimensional pathway created by projecting the three-dimensional CT-based model to a two-dimensional plane. The CT-based two-dimensional pathway and its associated angiography-based data may then be projected back to the three-dimensional CT-based model and displayed at the correct locations within the three-dimensional CT-based model.

In an exemplary aspect of the present disclosure, a co-registration system is provided. The co-registration comprises a processor circuit configured for communication with a display, an x-ray fluoroscopy device, and an intravascular catheter or guidewire, wherein the processor circuit is configured to: receive, from the x-ray fluoroscopy device, a plurality of x-ray fluoroscopy images of the blood vessel while the intravascular catheter or guidewire moves through the blood vessel; receive, from the intravascular catheter or guidewire, intravascular data representative of the blood vessel while the intravascular catheter or guidewire moves through the blood vessel; generate, using the plurality of x-ray fluoroscopy images, a first two-dimensional (2D) pathway of the blood vessel based on the intravascular catheter or guidewire moving through the blood vessel; generate a second 2D pathway of the blood vessel using a three-dimensional (3D) model of the blood vessel based on computed tomography (CT) imaging data; perform a first co-registration between the intravascular data and the second 2D pathway based on a mapping between corresponding locations of the first 2D pathway and the second 2D pathway; perform a second co-registration between the intravascular data and the 3D model based on the first co-registration; and output, to the display, the 3D model and a graphical representation of the intravascular data at a co-registered location of the 3D model.

In some aspects, the processor circuit is configured to: determine if the first 2D pathway and the second 2D pathway are comparable; and perform the first co-registration only in response to determining that the first 2D pathway and the second 2D pathway are comparable. In some aspects, the processor circuit is configured to: compute a similarity measure representative of if the first 2D pathway and the second 2D pathway are comparable; determine that the first 2D pathway and the second 2D pathway are comparable when the similarity measure satisfies a threshold. In some aspects, the processor circuit is configured to: generate a plurality of 2D pathways of the blood vessel using the 3D model of the blood vessel based on CT imaging data; and select a given 2D pathway of the plurality of 2D pathways as the second 2D pathway when the given 2D pathway and the first 2D pathway are comparable. In some aspects, the plurality of 2D pathways correspond to a plurality of angles for projecting the 3D model to a 2D plane. In some aspects, the processor circuit is configured to use an angle at which the plurality of x-ray fluoroscopy images were obtained to generate the second 2D pathway. In some aspects, the processor circuit is configured to compute a first projection of the 3D model to a 2D plane to generate the second 2D pathway. In some aspects, the processor circuit is configured to compute a second projection from the second 2D pathway to the 3D model to perform the second co-registration, wherein second projection is an inverse of the first projection. In some aspects, the intravascular data comprises at least one of pressure data, flow data, or imaging data. In some aspects, the co-registration system comprises the intravascular catheter or guidewire. In some aspects, the first 2D pathway and the second 2D pathway are representative of a same portion of the blood vessel.

In an exemplary aspect of the present disclosure, a co-registration system is provided. The co-registration system comprises a processor circuit configured for communication with a display and an x-ray angiography device, wherein the processor circuit is configured to: receive, from the x-ray angiography device, an x-ray angiography image of the blood vessel while the intravascular catheter or guidewire moves through the blood vessel; determine a metric representative of the blood vessel based on the x-ray angiography image; determine, using the x-ray angiography image, a first two-dimensional (2D) pathway of the blood vessel; generate a second 2D pathway of the blood vessel using a three-dimensional (3D) model of the blood vessel based on computed tomography (CT) imaging data; perform a first co-registration between the metric and the second 2D pathway based on a mapping between corresponding locations of the first 2D pathway and the second 2D pathway; perform a second co-registration between the metric and the 3D model based on the first co-registration; and output, to the display, the 3D model and a graphical representation of the metric at a co-registered location of the 3D model.

In some aspects, the processor circuit is configured to: determine if the first 2D pathway and the second 2D pathway are comparable; and perform the first co-registration only in response to determining that the first 2D pathway and the second 2D pathway are comparable. In some aspects, the processor circuit is configured to: compute a similarity measure representative of if the first 2D pathway and the second 2D pathway are comparable; determine that the first 2D pathway and the second 2D pathway are comparable when the similarity measure satisfies a threshold. In some aspects, the processor circuit is configured to: generate a plurality of 2D pathways of the blood vessel using the 3D model of the blood vessel based on CT imaging data; and select a given 2D pathway of the plurality of 2D pathways as the second 2D pathway when the given 2D pathway and the first 2D pathway are comparable. In some aspects, the plurality of 2D pathways correspond to a plurality of angles for projecting the 3D model to a 2D plane. In some aspects, the processor circuit is configured to use an angle at which the plurality of x-ray fluoroscopy images were obtained to generate the second 2D pathway. In some aspects, the processor circuit is configured to compute a first projection of the 3D model to a 2D plane to generate the second 2D pathway. In some aspects, the processor circuit is configured to compute a second projection from the second 2D pathway to the 3D model to perform the second co-registration, wherein second projection is an inverse of the first projection. In some aspects, the co-registration system comprises the x-ray angiography device. In some aspects, the first 2D pathway and the second 2D pathway are representative of a same portion of the blood vessel.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
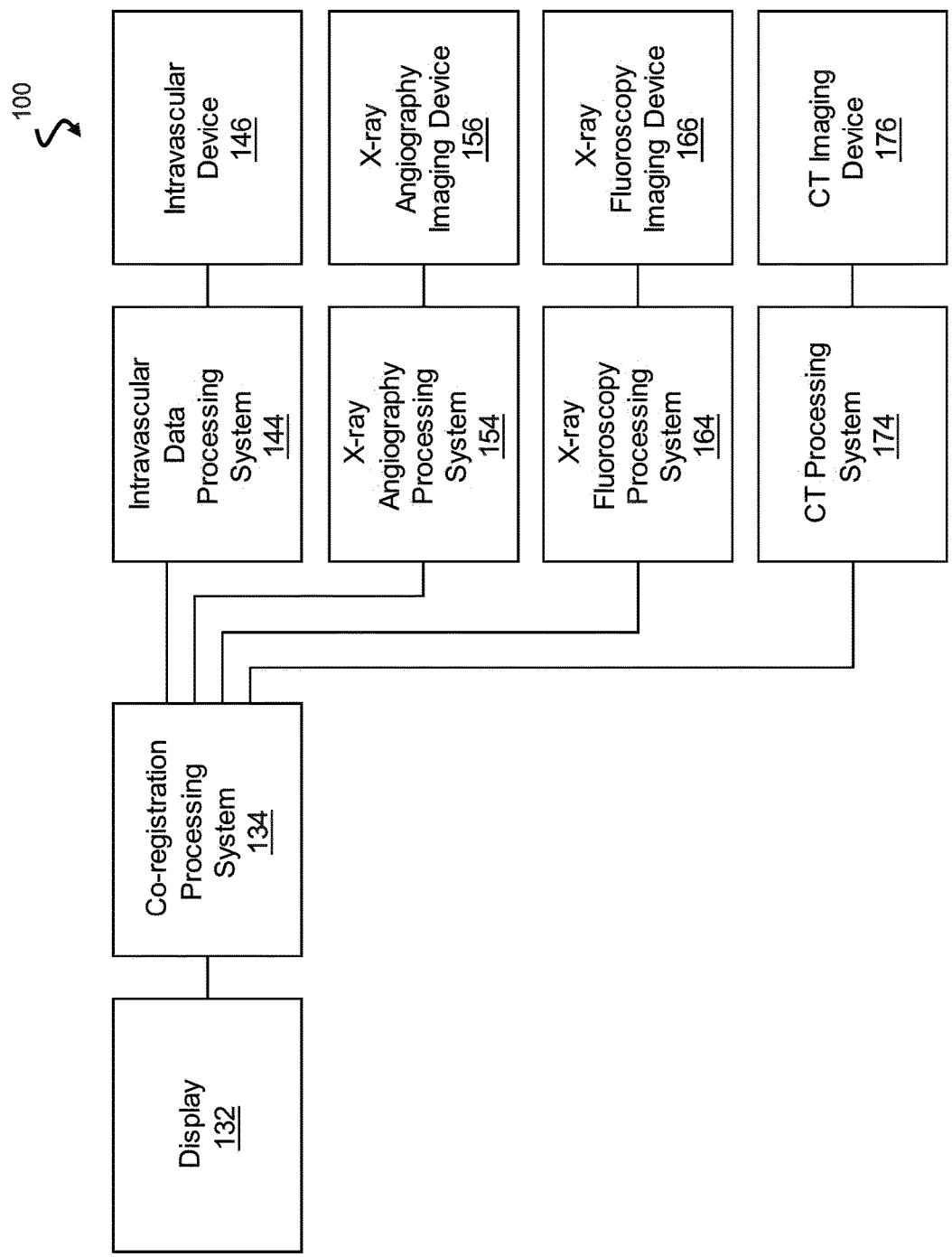
FIG. 1 is a schematic diagram of a medical diagnostic system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of a medical diagnostic system 100, according to aspects of the present disclosure. The diagnostic system 100 may include an intravascular device 146 in communication with an intravascular data processing system 144, an x-ray angiography imaging device 156 in communication with an x-ray angiography processing system 154, an x-ray fluoroscopy imaging device 166 in communication with an x-ray fluoroscopy processing system 164, and a computed tomography (CT) imaging device 176 in communication with a CT processing system 174. In addition, the diagnostic system 100 may include a co-registration processing system 134 in communication with the intravascular data processing system 144, the x-ray angiography processing system 154, the x-ray fluoroscopy processing system 164, and the CT processing system 174. The co-registration processing system 134 may additionally be in communication with a display 132 as well as any other suitable components, processors, systems, or devices. The diagnostic system 100 may be used for many different medical procedures, such as but not limited to diagnostic procedures, planning treatment, guiding treatment (e.g., during deployment of a treatment device), and evaluating the efficacy of treatment after it has been performed.

The co-registration processing system 134 shown in FIG. 1 may include any suitable hardware components, software components, or combinations of hardware and software components. For example, the processing system 134 may include any suitable circuitry, communication interfaces, processors, or processor circuits, among other components. In some embodiments, the processing system 134 may include one or more processor circuits substantially similar to the processor circuit 510 described with reference to FIG. 5. Any of the systems 144, 154, 164, and/or 174 may also include one or more processor circuits substantially similar to the processor circuit 510 described with reference to FIG. 5. Any of the systems 144, 154, 164, and/or 174 may also include similar features, components, hardware components, software components, or combinations thereof as that of the co-registration processing system 134 described.

The intravascular data processing system 144 may be configured to receive intravascular data collected with the intravascular device 146. The intravascular data processing system 144 may receive intravascular data via a connecting cable and/or a communication interface as will be discussed in more detail with reference to FIG. 2. In some embodiments, the processing system 144 may process the received intravascular data to reconstruct an image of the tissue structures in the medium surrounding the intravascular device 146. In other embodiments, the system 144 may process received intravascular data to calculate metrics relating to the medium surrounding the device 146 such as but not limited to the diameter of a body lumen, fluid pressure or flow within a body lumen, or other physiological data or metrics. The system 144 may also perform any other suitable calculations or measurements depending on the type of device 146 and the type of data received. The intravascular data processing system 144 may be in communication with the display 132 or another display. The intravascular data processing system 144 may display images, graphical representations, metrics, or other data relating to the body lumen imaged or measured via this display.

The x-ray angiography processing system 154 may be configured to receive angiography data collected with the x-ray angiography imaging device 156. The x-ray angiography processing system 154 may receive x-ray angiography data via a connecting cable and/or a communication interface. The angiography data can be used to generate angiographic images frames depicting the patient's anatomy. The angiography data obtained with the x-ray angiography imaging device 156 may correspond to an anatomy with a contrast agent introduced. The contrast agent may be used to enhance the visibility of internal fluids or structures within a patient's anatomy. In some embodiments, the contrast agent absorbs external x-rays from an x-ray source, resulting in decreased exposure on an x-ray detector in conjunction with the x-ray source. The contrast agent may be of any suitable material, chemical, or compound and may be a liquid, powder, paste, tablet, or of any other suitable form. For example, the contrast agent may include iodine-based compounds, barium sulfate compounds, gadolinium-based compounds, or any other suitable compounds. The contrast agent may additionally be referred to as a radiocontrast agent, a contrast dye, a radiocontrast dye, a contrast material, a radiocontrast material, a contrast media, or a radiocontrast media, among other terms.

In some embodiments, the processing system 154 may process the received angiography data to reconstruct an image of the patient anatomy and/or calculate metrics relating to the anatomy based on the angiography data. In some applications, the x-ray angiography processing system 154 may determine metrics associated with the patient anatomy using various image processing techniques or machine learning techniques as will be discussed in more detail hereafter with reference to FIG. 16. The x-ray angiography processing system 154 may be in communication with the display 132 or another display. The x-ray angiography processing system 154 may display images, graphical representations, metrics, or data to a user of the imaging system 100 via this display.

The x-ray fluoroscopy processing system 164 may be configured to receive fluoroscopy data collected with the x-ray fluoroscopy imaging device 166. In some embodiments, the x-ray fluoroscopy processing system 164 may be the same system as the x-ray angiography system 154 and the x-ray fluoroscopy imaging device 166 may be the same device as the x-ray angiography imaging device 164. However, the fluoroscopy imaging device 166 may obtain x-ray images of an anatomy without a contrast agent introduced to a patient's vasculature. In other embodiments, the x-ray fluoroscopy processing system 164 and the x-ray angiography processing system 154 are separate systems and the x-ray fluoroscopy imaging device 166 and the x-ray angiography imaging device 156 are separate devices. In either embodiment, the x-ray fluoroscopy processing system 164 may include any or all of the same features or characteristics of the x-ray angiography processing system 154 and the x-ray fluoroscopy imaging device 166 may include any or all of the same features or characteristics of the x-ray angiography imaging device 156. The fluoroscopy data can be used to generate fluoroscopic images frame depicting the patient's anatomy. In some instances, the fluoroscopic image frames can collectively form a video sequence of x-ray images.

The CT processing system 174 may be configured to receive CT data collected with the CT imaging device 176. The CT processing system 174 may receive CT data via a connecting cable and/or a communication interface. The CT data obtained with the CT imaging device 176 may correspond to an anatomy with contrast agent introduced or without contrast agent introduced. The contrast agent introduced to a patient's anatomy during a CT imaging procedure may be substantially similar to the contrast agent previously described in relation to the x-ray angiography imaging device 156 and processing system 154. In some embodiments, the processing system 174 may process the received CT data to reconstruct an image of the patient's anatomy or may reconstruct a three-dimensional model of the anatomy. In some applications, the CT processing system 174 may additionally determine metrics associated with the patient's anatomy using various image processing techniques or machine learning techniques. The CT processing system 174 may be in communication with the display 132 or another display. The CT processing system 174 may display images, 3D models, graphical representations, metrics, or data to a user via this display.

In some embodiments, the systems 134, 144, 154, 164, and/or 174 may each be a part of a combined system 100. For example, in some embodiments, the processing systems 134, 144, 154, 164, and/or 174 may all be positioned within the same enclosure or housing. In addition, the processing systems 134, 144, 154, 164, and/or 174 may share one or more software or hardware components. In other embodiments, the processing systems 134, 144, 154, 164, and/or 174 may be separate systems but may be in communication with one another. The processing systems may be in continuous communication with one another or may be in intermittent communication with one another. The processing systems may be in communication with the devices 145, 156, 166, 176, and/or the display 132 via one or more wired connecting cables including any suitable conductors, such as single conductors, twisted pairs, universal serial bus (USB) cables, or any other suitable connecting cables. The processing systems 134, 144, 154, 164, and/or 174 may additionally or alternatively be in communication or with the devices 145, 156, 166, 176, and/or the display 132 via a wireless connection, an optical connection, or may be in connection via any suitable type of movable memory or storage media, or via any other suitable means of communication. In some embodiments, the co-registration processing system 134 may receive data, including raw data and/or processed data, images, models, graphical representations, metrics, or any other information from any of the processing systems 144, 154, 164, and/or 174. The co-registration processing system 134 may receive such data from the other processing systems 144, 154, 164, and/or 174 simultaneously or separately. Any and/or all of the processing systems 134, 144, 154, 164, and/or 174 may include or be a part of any suitable system or device such as, but not limited to, a mobile console, a desktop computer, laptop computer, tablet, smartphone, or any other suitable computing device.

It is understood that aspects of the present disclosure may include any combination of extraluminal or extravascular imaging modalities such with x-ray angiography, x-ray fluoroscopy, computed tomography (CT), magnetic resonance imaging (MM), ultrasound, etc. For example, the CT processing system 174 and the CT imaging device 176 may be an Mill processing system and MM imaging device, or an ultrasound processing system and an ultrasound imaging device. In that regard, extraluminal or extravascular imaging be any suitable modality or modalities that can be used to generate 3D paths of anatomy (e.g., coronary vasculature).

Figure 2:
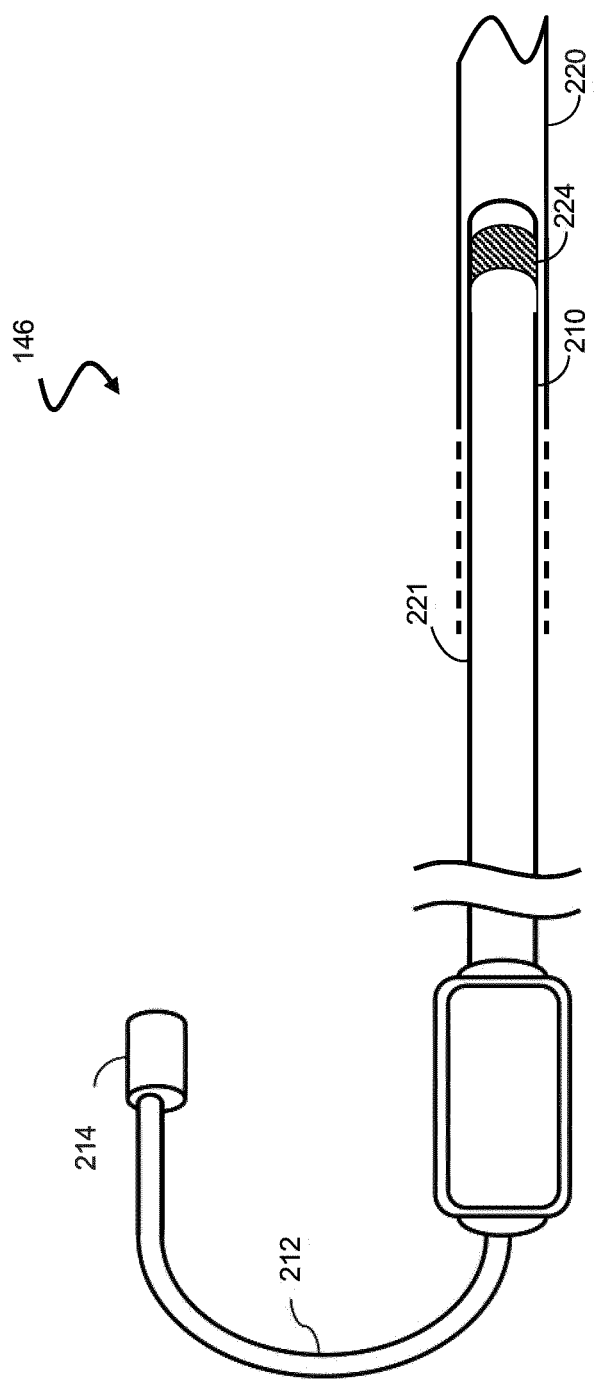
FIG. 2 is a diagrammatic view of an intravascular device, according to aspects of the present disclosure.

FIG. 2 is a diagrammatic view of an intravascular device 146, according to aspects of the present disclosure. The intravascular device 146 may be any type of invasive intravascular device used to acquire data from within the body of a patient. For example, the intravascular device 146 could be a catheter, a guide wire, or a guide catheter. In general, the device 146 can be an intraluminal device that obtains data from within any suitable lumen, chamber, or anatomy within the patient's body. An intraluminal device can also be referred to as an intra-body probe or an endo-cavity probe. The device 146 can be a sensing device that obtains information about the patient's body while positioned inside the patient's body. In some instances, the device 146 is an imaging device, such as an intravascular ultrasound (IVUS) device, including a rotational IVUS device or a solid-state IVUS device, an optical coherence tomography (OCT) device, an intravascular photoacoustic (IVPA) device, an intracardiac echocardiography device, or a transesophageal echocardiography (TEE) device. In some instances, the device 146 is a physiological-sensing device, such as a pressure-sensing device, a flow-sensing device, or a temperature-sensing device. The device 146 may include a flexible elongate member 221, a sensor assembly 210, a sensor 224, a transmission line bundle or cable 212, and a patient interface module (PIM) connector 214, among other components.

At a high level, the intravascular device 146 may acquire data relating to the region of anatomy surrounding the intravascular device 146. In that regard, the device 146 can be sized, shaped, or otherwise configured to be positioned within the body lumen 220 of a patient. In some embodiments, the system 100 may include a patient interface module (PIM) communicatively disposed between the intravascular device 146 and the intravascular data processing system 144 that receives and transfers the data obtained by the sensor 224 to the intravascular data processing system 144. The intravascular data processing system 144 can execute computer readable instructions stored on a non-transitory tangible computer readable medium.

The flexible elongate member 221 may be sized and shaped, structurally arranged, and/or otherwise configured to be positioned within a body lumen 220 of a patient. The flexible elongate member 221 may be a part of guidewire and/or a catheter (e.g. an inner member and/or an outer member). The flexible elongate member 221 may be constructed of any suitable flexible material. For example, the flexible elongate member 221 may be constructed of a polymer material including polyethylene, polypropylene, polystyrene, or other suitable materials that offer flexibility, resistance to corrosion, and lack of conductivity. In some embodiments, the flexible elongate member 221 may define a lumen for other components to pass through. The flexible elongate member 221 may be sufficiently flexible to successfully maneuver various turns or geometries within the vasculature of a patient. The flexible elongate member 221 may be of any suitable length or shape and may have any suitable characteristics or properties.

The sensor assembly 210 may be coupled to the flexible elongate member 221 and positioned at a distal portion or a distal end of the flexible elongate member 221. The sensor assembly 210 may house various circuitry, sensors, transducers, or any other suitable components used to acquire intravascular data. For example, the sensor assembly may include a support member, unibody, sensor housing, sensor mount, pressure sensor, flow sensor, temperature sensor, transducer array, control logic dies, various circuits, flexible substrates, various adhesives, or backing material, among other components. The sensor assembly 210 may provide structural support to components within the intravascular imaging device 146. The sensor assembly 210 may be constructed of any suitable material, including flexible or inflexible materials. The sensor assembly 210 may be of any suitable shape, including a tubular or circular shape, as well as any other geometric or non-geometric shape.

The sensor assembly 210 can acquire data relating to the lumen in which the device 146 is positioned. The sensor assembly 210 may acquire this data via any suitable number or type of sensors or other measurement tools. The data obtained by the intravascular device 146 and/or the sensor 224 data may be of any suitable form. In some embodiments, the sensor 224 is an ultrasound transducer or ultrasound transducer array. The sensor 224 can include one or more ultrasound transducer elements that emit ultrasonic energy and receive echoes that can be used to generate an ultrasound image (e.g., an IVUS image). In another embodiment, the sensor 224 is a pressure sensor that acquires pressure data at one or more locations along the body lumen of the patient as the device 146 moves through the body lumen. Pressure data can be used by the processing system 144 to calculate fractional flow reserve (FFR), instantaneous wave-free ratio (iFR), Pd/Pa, and/or any other suitable pressure ratio. In another embodiment, the sensor 224 is a flow sensor that obtains data related to velocity and/or volume of blood flow within a blood vessel. Flow data can be used by the processing system 144 to calculate coronary flow reserve (CFR), and/or any other suitable flow metric. For example, the flow sensor 224 can be a Doppler ultrasound transducer element. In another embodiment, the sensor 224 is a temperature sensor that obtains temperature data within the body lumen. In other embodiments, the sensor 224 may acquire OCT imaging data, IVPA imaging data, or any other suitable data.

The sensor 224 shown in FIG. 2 may be any suitable type of sensor depending on the specific application or type of intravascular device 146 including any of the components for intravascular data acquisition previously listed. In addition, the sensor 224 may represent more than one sensor. For example, in some embodiments, the sensor 224 may include multiple sensor devices including 2, 4, 6, 8, 16, 32, 64, 128, or more sensors, or any suitable number therebetween. In some embodiments, the sensor 224 may include a transducer array. The sensor 224 may additionally be a single rotating transducer. In some embodiments, the sensor 224 may be one or more pressure sensors and one or more flow sensors. The sensor 224, although positioned at a distal region of the sensor assembly 210 and the flexible elongate member 221, may be positioned at any suitable location on or within the sensor assembly 210 or the flexible elongate member 221.

The flexible elongate member 221 and/or the cable 212 include one, two, three, four, five, six, seven, or more conductors, optical fibers, or other signal communication lines. The signal communication lines are communicatively coupled to the connector 214 and the sensor 224. The signal communication lines carry electrical signals, optical signals, and/or any suitable type of signal from the sensor 224 to the processing system 144 (e.g., data obtained by the sensor 224) and/or from the processing system 114 to the sensor 224 (e.g., command/control signals). The cable 212 may facilitate communication between the intravascular device 146 and the intravascular data processing system 144 or any other control system or host system.

The cable 212 may be coupled to the patient interface module (PIM) connector 214 at a proximal portion or proximal end of the intravascular device 146. The PIM connector 214 may communicatively couple the signal communication lines to the PIM or other interface in communication with the intravascular data processing system 144. The PIM connector 214 may also physically couple the intravascular device 146 to the PIM.

In some embodiments, the intravascular device 146 and/or the PIM may perform preliminary processing of the intravascular data prior to relaying the data to the processing system. In examples of such embodiments, the intravascular device 146 and/or the PIM may perform amplification, filtering, and/or aggregating of the data. In an embodiment, the intravascular data processing system 144 may also supply high- and low-voltage DC power to support operation of the device 146 and/or the PIM including circuitry within the device.

Figure 3:
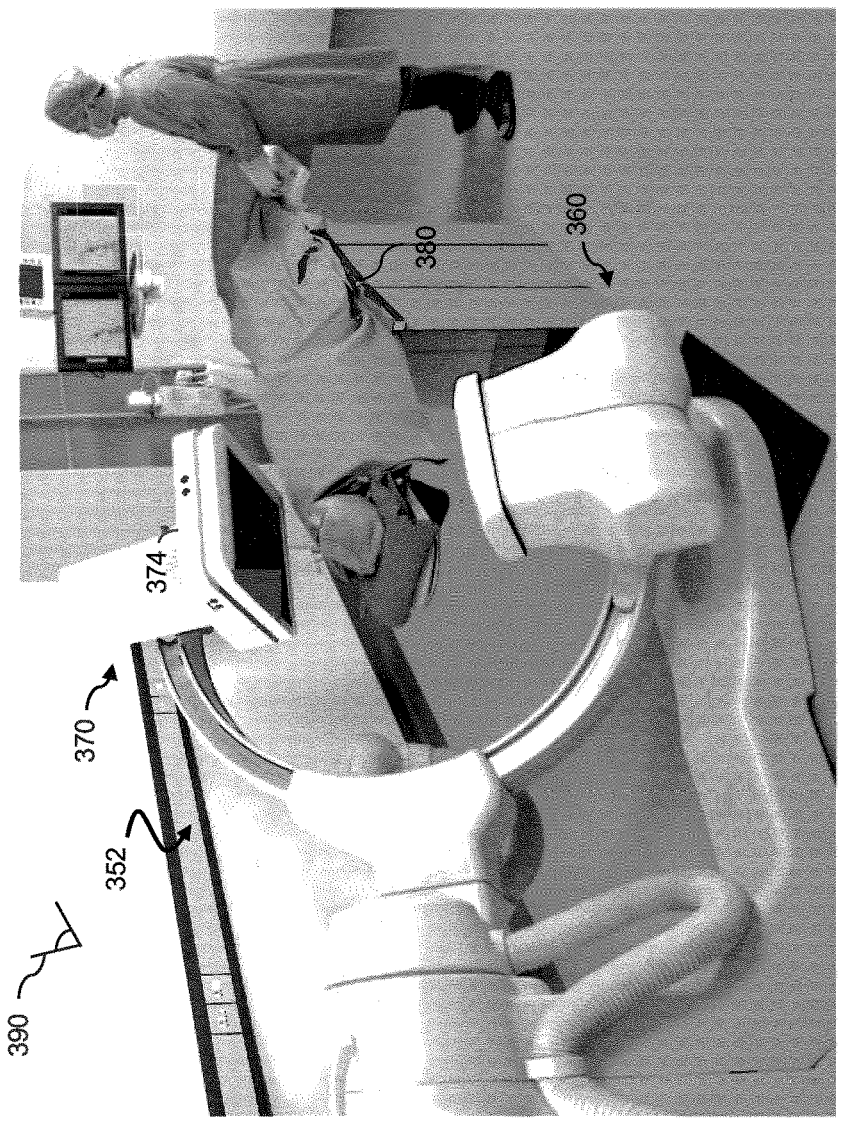
FIG. 3 is a diagrammatic view of an x-ray imaging device, according to aspects of the present disclosure.

FIG. 3 is a diagrammatic view of an x-ray imaging device 300, according to aspects of the present disclosure. The x-ray imaging device 300 may be the x-ray angiography imaging device 156 (FIG. 1) or may be the x-ray fluoroscopy imaging device 166 (FIG. 1) or may be a different device. In some embodiments, the x-ray imaging device 300 shown in FIG. 3, the x-ray angiography imaging device 156, and the x-ray fluoroscopy imaging device 166 may be the same device. The x-ray imaging device 300 may be of any suitable type, for example, it may be a stationary x-ray system such as a fixed c-arm x-ray device, a straight arm x-ray device, or a w-arm device. The x-ray imaging device 300 may additionally be any suitable mobile device such as a mobile c-arm x-ray device. The x-ray imaging device 300 may also be in communication with the x-ray angiography imaging processing system 154 and/or the x-ray fluoroscopy processing system 164. In some embodiments, the x-ray device 300 may include a digital radiography device or any other suitable device.

The x-ray imaging device 300 as shown in FIG. 3 includes an x-ray source 360, a detector 370 including an x-ray input screen 374. The x-ray source 360 and the input screen 374 may be mounted at a mutual distance and mounted on a movable arm 352. Positioned between the x-ray source 360 and the x-ray detector 370 may be an anatomy of a patient or object 380. The x-ray imaging device 300 may be used to image any suitable location or region of a patient's anatomy, including tissues, organs, malignancies, or any other structures or features. For example, the x-ray imaging device 300 may image without limitation the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. The imaging device 300 may additionally image tumors, cysts, lesions, hemorrhages, or blood pools, muscle, blood, blood plasma, interstitial fluid, lymph plasma, cerebrospinal fluid, intraocular fluid, serous fluid, synovial fluid, digestive fluid, urinary fluid, amniotic fluid, or any other type of suitable fluid, or any other region, structure, fluid, or gas within a patient anatomy.

The x-ray source 360 may include an x-ray tube adapted to generate x-rays. Some aspects of the x-ray source 360 may include one or more vacuum tubes including a cathode in connection with the negative lead of a high-voltage power source and an anode in connection with the positive lead of the same power source. The cathode of the x-ray source 360 may additionally include a filament. The filament may be of any suitable type or constructed of any suitable material, including tungsten or rhenium tungsten, and may be positioned within a recessed region of the cathode. One function of the cathode may be to expel electrons from the high voltage power source and focus them into a well-defined beam aimed at the anode. The anode may also be constructed of any suitable material and may be configured to create x-radiation from the emitted electrons of the cathode. In addition, the anode may dissipate heat created in the process of generating x-radiation. The anode may be shaped as a beveled disk and, in some embodiments, may be rotated via an electric motor. The cathode and anode of the x-ray source 360 may be housed in an airtight enclosure, sometimes referred to as an envelope.

In some embodiments, the x-ray source 360 may include a radiation object focus which influences the visibility of an image. The radiation object focus may be selected by a user of the system 100 or by a manufacturer of the system 100 based on characteristics such as blurring, visibility, heat-dissipating capacity, or other characteristics. In some embodiments, an operator or user of the system 100 may switch between different provided radiation object foci in a point-of-care setting.

The detector 370 may be configured to acquire x-ray images and may include the input screen 374. The input screen 374 may include one or more intensifying screens configured to absorb x-ray energy and convert the energy to light. The light may in turn expose a film. The input screen 374 may be used to convert x-ray energy to light in embodiments in which the film may be more sensitive to light than x-radiation. Different types of intensifying screens within the image intensifier may be selected depending on the region of a patient to be imaged, requirements for image detail and/or patient exposure, or any other factors. Intensifying screens may be constructed of any suitable materials, including barium lead sulfate, barium strontium sulfate, barium fluorochloride, yttrium oxysulfide, or any other suitable material. The input screen 374 may be a fluorescent screen or a film positioned directly adjacent to a fluorescent screen. In some embodiments, the input screen 374 may also include a protective screen to shield circuitry or components within the detector 370 from the surrounding environment. The x-ray detector 370 may additionally be referred to as an x-ray sensor.

The object 380 may be any suitable object to be imaged. In an exemplary embodiment, the object 380 may be the anatomy of a patient including any region of a patient's anatomy previously mentioned. More specifically, the anatomy to be imaged may include the coronary region. In some embodiments, the object 380 may include man-made structures.

In some embodiments, the x-ray source 360 and x-ray detector 370 are mounted to the movable arm 352. In this configuration, the x-ray source 360 and the x-ray detector 370 may be rotated around the object 380 or patient anatomy to acquire images of the object 380 or patient anatomy at different angles. The movable arm 352 may move the x-ray source 360 and detector 370 to any suitable location around the object 380 or patient anatomy. In some embodiments, the movable arm 352 may receive commands from the system 154 or 164 based on a user input to move the x-ray source 360 and detector 370 to a desired position or angle 390 with respect to the object 380 or patient anatomy to be imaged. The arm 352 may be of any suitable type or shape in addition to the one shown in FIG. 3 and may additionally be referred to as a gantry. In some embodiments, the x-ray imaging device 300 may include more than one set of x-ray sources 360 and detectors 370. For example, the x-ray imaging device 300 may be a bi-plane x-ray imaging system. In embodiments in which the x-ray imaging device 300 includes multiple sets of x-ray sources 360 and corresponding x-ray detectors 370, a physician may image the same regions of a patient's anatomy from multiple angles simultaneously or may image different regions of the patient's anatomy simultaneously.

As previously mentioned, the x-ray imaging device 300 may be configured to acquire angiography images. In such embodiments, a contrast agent may be introduced to a patient's anatomy before imaging. The contrast agent may be used to enhance the visibility of internal structures within a patient's anatomy. The contrast agent may absorb external x-rays, resulting in decreased exposure on the x-ray detector 370. The contrast agent may be of any suitable type previously listed. In other embodiments, in which fluoroscopy images are to be obtained, a contrast agent may not be introduced to the patient anatomy prior to imaging.

When an x-ray processing system, such as the x-ray angiography processing system 154 or the x-ray fluoroscopy processing system 164 of FIG. 1, is in communication with the x-ray imaging device 300, various data may be transmitted. This communication includes x-ray imaging data as well as control commands to the x-ray source 360 and/or x-ray detector 370 of the x-ray device 300. In some embodiments, the x-ray imaging device 300 may perform preliminary processing of the x-ray data prior to relaying the data to the processing system. In examples of such embodiments, the x-ray imaging device 300 may perform amplification, filtering, and/or aggregating of the data. In an embodiment, the x-ray image processing system may also supply high- and low-voltage DC power to support operation of the device 300 including circuitry within the device.

Figure 4:
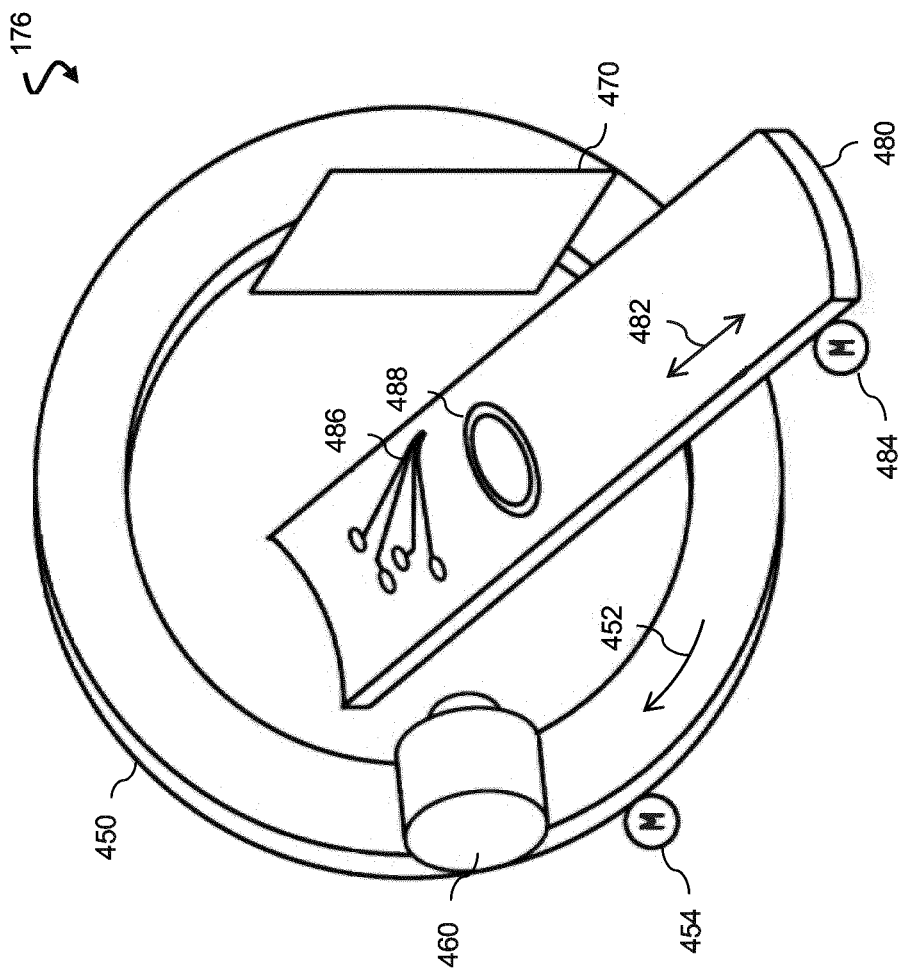
FIG. 4 is a diagrammatic view of a computed tomography (CT) imaging device, according to aspects of the present disclosure.

FIG. 4 is a diagrammatic view of a computed tomography (CT) imaging device 176, according to aspects of the present disclosure. The CT imaging device 176 may include an x-ray source 460, an x-ray detector 470, a CT gantry 450, a rotary drive 454, a patient support 480, a drive 484, a cardiac monitor 486, and a respiratory monitor 488, among other components. The CT imaging device 176 may be of any suitable form or type. For example, the CT imaging device 176 may be a spiral CT scanner, a single slice CT scanner, a multi-slice CT scanner, such as a 2, 4, 6, 8, 16, 32, 40, 64, or 128 slice CT scanner or greater slice numbers or a CT scanner of slice numbers therebetween. The CT imaging device 176 may also be a fixed or mobile device. The CT imaging device 176 may additionally have any suitable rotation time, slice width, or any other characteristics or features.

The x-ray source 460 may be substantially similar to the x-ray source 360 of FIG. 3 in that it may be configured to produce and project x-radiation. Specifically, the x-ray source 460 may include an x-ray tube and may include one or more vacuum tubes including a cathode and an anode in connection with a high-voltage power source. The cathode and anode of the x-ray source 460 may be configured to create x-radiation. The cathode and anode of the x-ray source 460 may be housed in an airtight enclosure and mounted to the CT gantry 450. The x-ray source 460 may also include a radiation object focus similar to the x-ray source 360.

The x-ray detector 470 may also be substantially similar to the x-ray detector 370 of FIG. 3. The detector 470 may be configured to acquire x-ray images and may include an input screen similar to the input screen 374 and/or one or more intensifying screens as previously described with reference to FIG. 3. Components within the x-ray detector 470 are configured to absorb x-ray energy and convert the energy to form an image. The x-ray detector 470 may include a fluorescent screen or a film positioned directly adjacent to a fluorescent screen.

The x-ray source 460 and the x-ray detector 470, along with various other components, may be mounted to the CT gantry 450 as shown in FIG. 4. The CT gantry 450 may be configured to rotate around a patient, an object, or the patient support 480 shown. The CT gantry 450 may rotate in a direction shown by arrow 452 or in another direction. As the CT gantry 450 rotates around a central region, the x-ray source 460 may emit x-radiation toward and/or through a patient anatomy. The x-ray detector 470 may be positioned opposed to and equidistant from the x-ray source 460 with relation to the patient anatomy to be imaged and may receive x-radiation emitted by the x-ray source 460. The CT imaging device 176 may be configured to image any suitable anatomical regions or locations, including any structures or features within a patient anatomy previously mentioned with regards to the x-ray imaging device 300. Because different structures within a patient anatomy absorb x-radiation differently, differences in absorption may be detected by the x-ray detector 470 and used to reconstruct an image of the anatomy. The x-ray source 460 and/or the x-ray detector 470 may be configured to obtain x-ray data at any suitable sample rate. X-ray data may be obtained from any suitable location or angle around the central region or patient support 480 and used to reconstruct an image of the patient anatomy.

The CT gantry 450 may rotate at any suitable rate. For example, the CT gantry may rotate at a rate of 60, 120, 200, 400 revolutions per minute (rpm) or more, or any suitable rate of rotation therebetween. In embodiments in which a heart is to be imaged, a greater rate of rotation may be used. The CT gantry 450 may additionally include other components configured to produce, receive, or process x-radiation data or images. For example, the CT gantry 450 may include an inverter, a collimator, a cooling system of any suitable type, additional sensors or detectors, or a multiplier, among other components.

The CT gantry 450 may be coupled to the rotary drive 454. The rotary drive 454 may be configured to rotate the CT gantry 450 in the manner previously described. The rotary drive 454 may be in communication with the CT processing system 174 (FIG. 1) or another control system of any suitable type. For example, the rotary drive 454 may receive command signals from a control system. An operator of the CT imaging device 176 may select the rate of rotation of the CT gantry 450 and/or the sample rate of the x-ray source 460 and detector 470.

The patient support 480 may be positioned along a longitudinal axis 482 in relation to the CT gantry 450. The patient support 480 may be configured to support a patient to be imaged and move along the longitudinal axis or direction 482 so as to move the patient anatomy to be imaged through the CT gantry 450. The patient support 480 may be configured to move a specified distance corresponding to the region of the patient to be imaged. The drive 484 may be coupled to the patient support 480 and be configured to move the patient support the specified distance through the center of the CT gantry 450.

In some embodiments, the patient support 480 may include one or more patient monitors configured to monitor metrics or vital signs of the patient anatomy as the patient anatomy is imaged. For example, the cardiac monitor 486 may monitor and track the cardiac cycle of a patient. The cardiac monitor 486 may be of any suitable type, such as an electrocardiography (EKG) lead system, or other type of monitor. In addition, the patient support 480 may include the respiratory monitor 488. The respiratory monitor 488 may be configured to monitor and track a patient's respiration state. Additional patient monitors may be included within the patient support 480.

Figure 5:
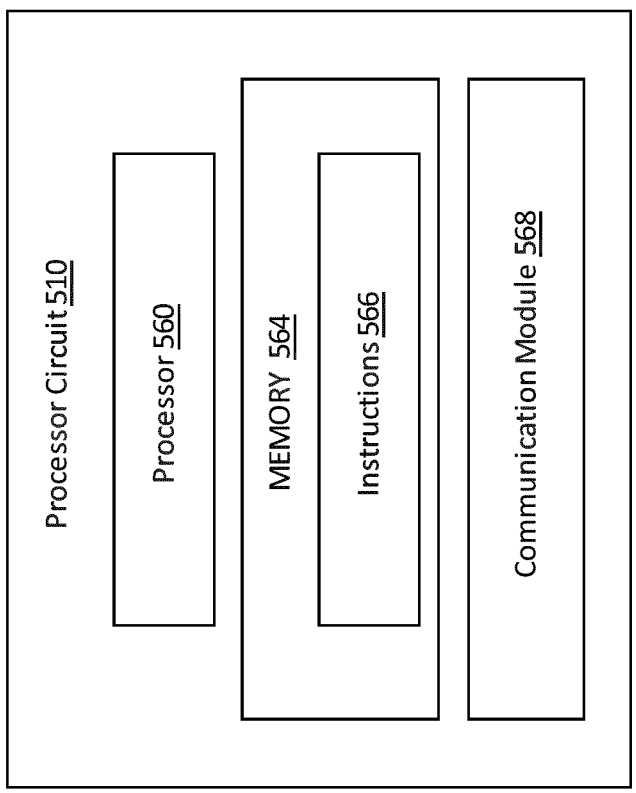
FIG. 5 is a schematic diagram of a processor circuit, according to aspects of the present disclosure.

FIG. 5 is a schematic diagram of a processor circuit 510, according to aspects of the present disclosure. The processor circuit 510 or a similar processor circuit may be implemented in any suitable device or system previously disclosed. One or more processor circuits 510 can be configured to perform the operations described herein. The processor circuit 510 can include additional circuitry or electronic components, such as those described herein. In an example, one or more processor circuits 510 may be in communication with transducer arrays, sensors, circuitry, or other components within the intravascular device 146 (FIGS. 1, 2), the x-ray source 360, the input screen 374, circuitry, or any other components within the x-ray imaging device 300 (FIG. 3) or angiography device 156 or fluoroscopy device 166 (FIG. 1). One or more processor circuits 510 may also be in communication with the x-ray source 460, the x-ray detector 470, circuitry, or any other components within the CT imaging device 176 (FIGS. 1, 4) and/or the display 132 (FIG. 1), as well as any other suitable component or circuit within the diagnostic system 100. As shown, the processor circuit 510 may include a processor 560, a memory 564, and a communication module 568. These elements may be in direct or indirect communication with each other, for example via one or more buses.

The processor 560 may include a CPU, a GPU, a DSP, an application-specific integrated circuit (ASIC), a controller, a field programmable gate array (FPGA), another hardware device, a firmware device, or any combination thereof configured to perform the operations described herein. The processor 560 may also be implemented as a combination of computing devices, e.g., a combination of a DSP and a microprocessor, a plurality of microprocessors, one or more microprocessors in conjunction with a DSP core, or any other such configuration.

The memory 564 may include a cache memory (e.g., a cache memory of the processor 560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 564 includes a non-transitory computer-readable medium. The memory 564 may store instructions 566. The instructions 566 may include instructions that, when executed by the processor 560, cause the processor 560 to perform the operations described herein with reference to the devices 146, 156, 166, 300, 176, and/or the systems 134, 144, 154, 164, and/or 174. Instructions 566 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 568 can include any electronic circuitry and/or logic circuitry to facilitate direct or indirect communication of data between the processor circuit 510, the previously described devices and systems, and/or the display 132. In that regard, the communication module 568 can be an input/output (I/O) device. In some instances, the communication module 568 facilitates direct or indirect communication between various elements of the processor circuit 510 and/or the devices and systems of the diagnostic system 100 (FIGS. 1-4).

Figure 6:
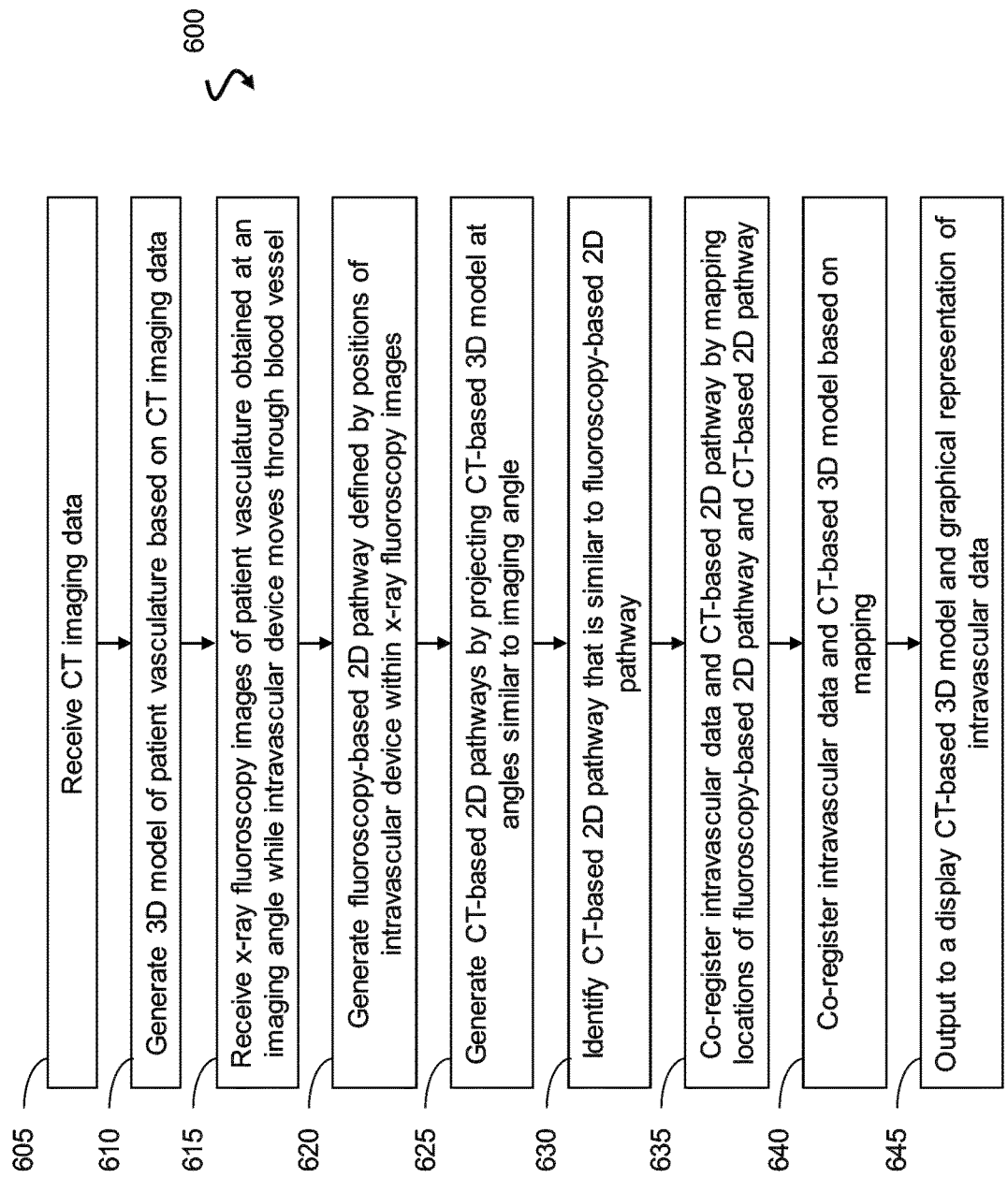
FIG. 6 is a flow diagram of a method of co-registering intravascular data with a CT-based 3D model, according to aspects of the present disclosure.

FIG. 6 is a flow diagram of a method 600 of co-registering intravascular data with a CT-based 3D model, according to aspects of the present disclosure. One or more steps of the method 600 will be described with reference to FIGS. 8-14. As illustrated, the method 600 includes a number of enumerated steps, but embodiments of the method 600 may include additional steps before, after, or in between the enumerated steps. In some embodiments, one or more of the enumerated steps may be omitted, performed in a different order, or performed concurrently. The steps of the method 600 can be carried out by any suitable component within the diagnostic system 100 and all steps need not be carried out by the same component. In some embodiments, one or more steps of the method 600 can be performed by, or at the direction of, a processor circuit of the diagnostic system 100, including, e.g., the processor 560 (FIG. 5) or any other component.

An advantage of co-registering data from different medical diagnostic modalities includes providing a user of the system 100 with accurate information relating to the position of an intravascular device 146 within the patient anatomy. The method 600 includes providing location information of the intravascular device 146 and measurements or data obtained by the device 146 in conjunction with a three-dimensional CT-based model. A user of the system 100 may then view exact location information corresponding to intravascular measurements relating to a blood vessel as a graphical representation overlaid on or otherwise in conjunction with a CT-based model. In this way, the user of the imaging system 100 need not estimate the location of measurements from an intravascular device 146 based on separate views of an x-ray image and/or measurement display.

At step 605, the method 600 includes receiving CT imaging data. The CT imaging data may be obtained via the CT imaging device 176 and CT processing system 174 (FIG. 1) previously described or with any other similar device and processing system. The CT imaging data may correspond to an anatomy of any suitable region or structure of a patient including any of the previously mentioned parts of a patient anatomy. In some embodiments, the CT imaging data may correspond to the vasculature of a heart acquired through a CT scanning procedure or CT scan. In some imaging procedures, a contrast agent may be introduced to the patient vasculature. The anatomy may also be imaged with the CT imaging device 176 without a contrast agent introduced to the vasculature. In procedures in which a heart is to be imaged, a contrast agent may be introduced to the coronary vasculature. As previously described, the CT imaging device 176 may acquire the CT imaging data by rotating the x-ray source 460 and the x-ray detector 470 mounted to the CT gantry 450 (FIG. 4) around the patient anatomy and acquiring x-ray imaging data at various angles in relation to the patient anatomy and across various regions of the patient anatomy.

Figure 8:
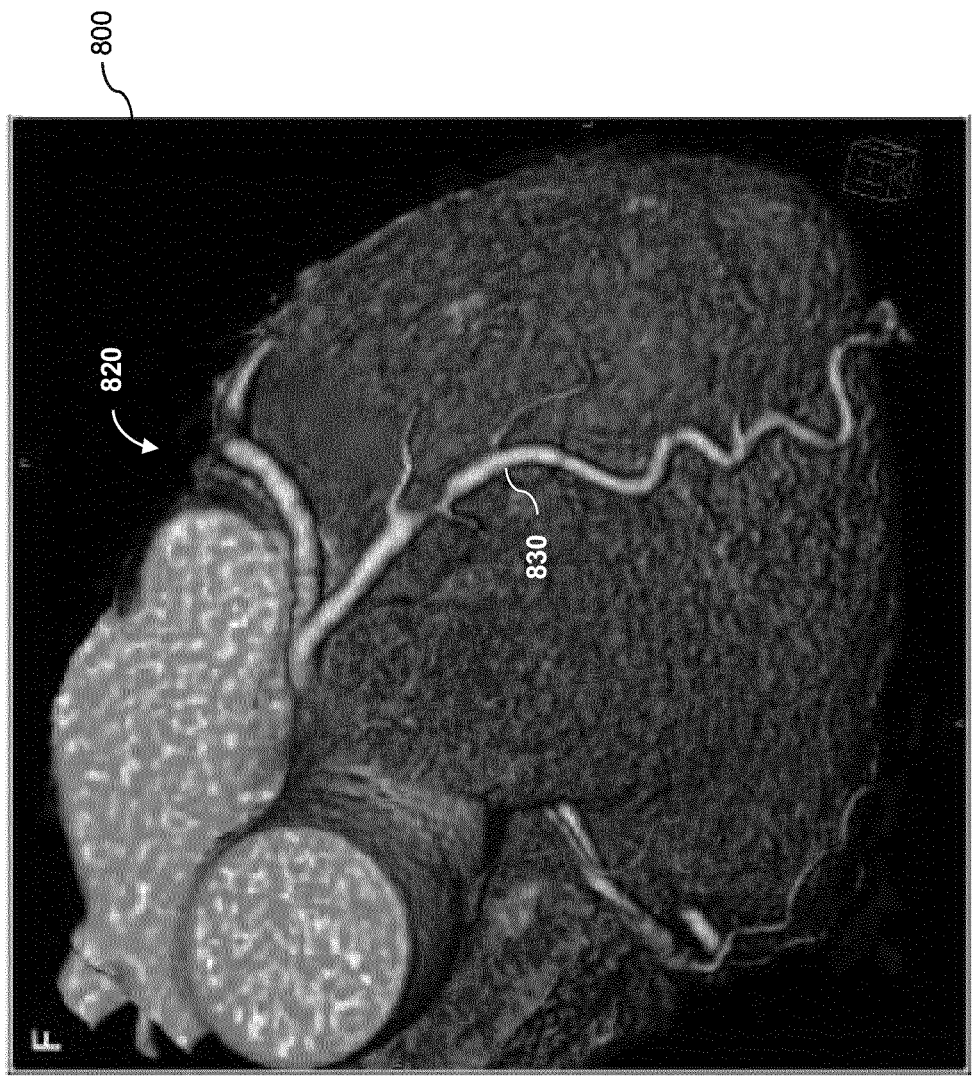
FIG. 8 is a diagrammatic view of a coronary CT-based 3D model, according to aspects of the present disclosure.
Figure 8:
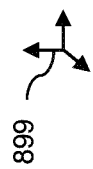

At step 610, the method 600 includes generating a three-dimensional model 800 of the patient's vasculature based on the CT imaging data. Step 610 will be described with reference to FIG. 8, which is a diagrammatic view of a CT-based 3D model 800 of a heart 820, according to aspects of the present disclosure. As shown by the axes 899 adjacent to the model 800, the model 800 is a three-dimensional object and may be viewed from any suitable angle in three-dimensional space. FIG. 8 depicts an example image of a coronary CT scan of an entire heart of a patient visualized as a three-dimensional model. The CT processing system 174 may use the CT imaging data obtained at step 605 with the CT imaging device 176 (FIG. 1) to reconstruct multiple two-dimensional images or slices of the patient anatomy. In some embodiments, these two-dimensional images may correspond to locations along the longitudinal axis 482 of the patient anatomy or the patient support 480 (FIG. 4). For example, one two-dimensional image may correspond to a cross-sectional slice of the patient anatomy at location along the longitudinal axis 482. These generated two-dimensional images may then be combined to construct a three-dimensional model of the anatomy, similar to the three-dimensional CT-based model 800 shown in FIG. 8. As shown in FIG. 8, the heart 820 imaged and displayed includes multiple vessels 830 extending along the surface of the heart. Features may be observed in great detail in the CT-based model 820 as well as viewed from various angles.

Figure 10:
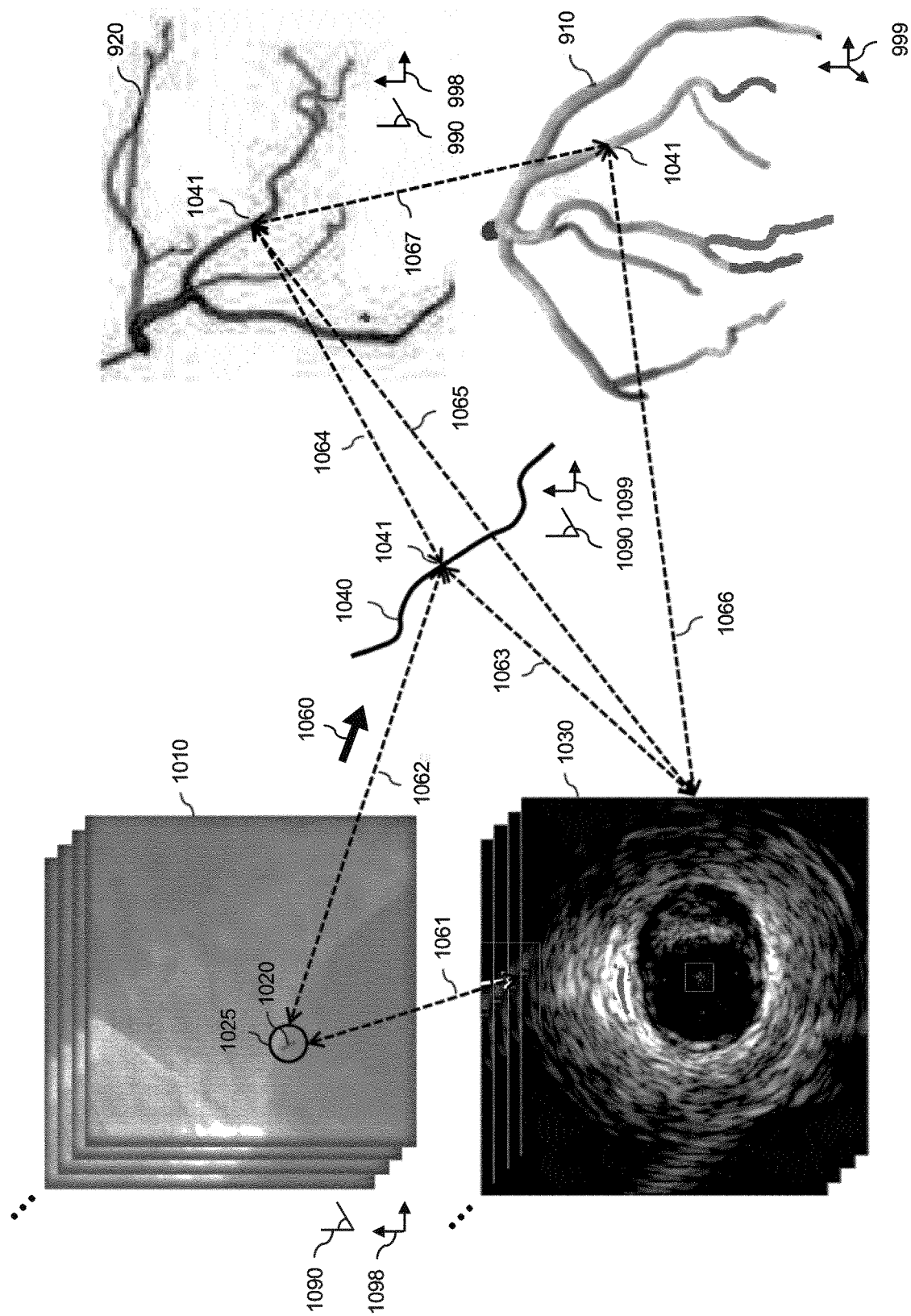
FIG. 10 is a diagrammatic view of a relationship between x-ray fluoroscopy images, intravascular data, a fluoroscopy-based 2D pathway defined by the motion of an intravascular device, a CT-based 2D pathway, and a CT-based 3D model, according to aspects of the present disclosure.

At step 615, the method 600 includes receiving x-ray fluoroscopy images 1010 of the patient vasculature obtained at an imaging angle 1090 while an intravascular device 1020 moves through a blood vessel 830. Step 615 will be described with reference to FIG. 10. FIG. 10 is a diagrammatic view of a relationship between x-ray fluoroscopy images 1010, intravascular data 1030, a fluoroscopy-based 2D pathway 1040 defined by the motion of an intravascular device 1020, a CT-based 2D pathway 920, and a CT-based 3D model 910, according to aspects of the present disclosure.

At step 615, the patient anatomy may be imaged with an x-ray device while a physician performs a pullback with an intravascular device 1020 such that the intravascular device 1020 moves through a blood vessel of the anatomy. The x-ray device used to obtain the fluoroscopy images 1010 may be substantially similar to the x-ray device 300 of FIG. 3 or the x-ray fluoroscopy imaging device 166 of FIG. 1. In some embodiments, the fluoroscopy images 1010 may be obtained while no contrast agent is present within the patient vasculature. Such an embodiment is shown by the fluoroscopy images 1010 in FIG. 10. The radiopaque portion of the intravascular device 1020 is visible within the displayed fluoroscopy image 1010 as indicated by the circle 1025. The fluoroscopy images 1010 may correspond to a continuous image stream of fluoroscopy images and may be obtained as the patient anatomy is exposed to a reduced dose of x-radiation. It is noted that the fluoroscopy images 1210 may be acquired with the x-ray source 360 and the x-ray detector 370 positioned at any suitable angle in relation to the patient anatomy. This angle is shown by angle 1090. In addition, as shown by the axes 1098, the fluoroscopy images 1010 are two-dimensional.

The intravascular device 1020 may be any suitable intravascular device. The device may be substantially similar to the device 146 of FIGS. 1 and 2, including any of its described embodiments. As the intravascular device 1020 moves through the patient vasculature, the x-ray imaging system may acquire multiple fluoroscopy images 1010 showing the radiopaque portion of the intravascular device 1020. In this way, each fluoroscopy image 1010 shown in FIG. 10 may depict the intravascular device 1020 positioned at a different location such that the x-ray system may track the position of the intravascular device 1020 over time.

As the intravascular device 1020 is pulled through the patient vasculature, it may acquire intravascular data 1030. In an example, the intravascular data 1030 shown in FIG. 10 may be IVUS images. However, the intravascular data may be any suitable data, including IVUS images, FFR data, iFR data, OCT data, or any other measurements or metrics relating to blood pressure, blood flow, lumen diameter, or other physiological data acquired during a pullback of an intravascular device.

As the physician pulls the intravascular device 1020 through the patient vasculature, the system 100 may co-register the intravascular data 1030 to the fluoroscopy images 1010, as indicated by the arrow 1061. In this way, each intravascular measurement acquired by the intravascular device 1020 may be associated with a position within the patient anatomy. For example, the first IVUS image 1030 shown in FIG. 10 may be associated with the first fluoroscopy image 1010. The first IVUS image 1030 may be an image acquired by the intravascular device 1020 at a position within the vasculature and within the first fluoroscopy image 1010 as shown by the circle 1025. Similarly, an additional IVUS image 1030 may be associated with an additional fluoroscopy image 1010 showing the intravascular device 1020 at a new location within the image 1010.

Any suitable number of IVUS images or other intravascular data 1030 may be acquired during an intravascular device pullback and any suitable number of fluoroscopy images 1010 may be obtained. In some embodiments, there may be a one-to-one ratio of fluoroscopy images 1010 and intravascular data 1030. In other embodiments, there may be differing numbers of fluoroscopy images 1010 and/or intravascular data 1030. The process of co-registering the intravascular data 1030 with the fluoroscopy images 1010 at step 630 may include some features similar to those described in U.S. Pat. No. 7,930,014, titled, "VASCULAR IMAGE CO-REGISTRATION," and filed Jan. 11, 2006, which is hereby incorporated by reference in its entirety. The co-registration process may also include some features similar to those described in U.S. Pat. Nos. 8,290,228, 8,463,007, 8,670,603, 8,693,756, 8,781,193, 8,855,744, and 10,076,301, all of which are also hereby incorporated by reference in their entirety.

At step 620, the method 600 includes generating a fluoroscopy-based 2D pathway 1040 defined by the positions of the intravascular device 1020 within the x-ray fluoroscopy images 1010. Step 620 will also be described with reference to FIG. 10. In some embodiments, the fluoroscopy-based 2D pathway 1040 may additionally be referred to as a roadmap, a roadmap image, a path, or any other suitable term.

The different positions of the intravascular device 1020 as shown in the fluoroscopy images 1010 may define a fluoroscopy-based two-dimensional pathway 1040, as shown by the arrow 1060. The fluoroscopy-based 2D pathway 1040 reflects the path of the intravascular device 1020 as it moved through the patient vasculature. The fluoroscopy-based 2D pathway 1040 defines the path as measured by the x-ray device which acquired the fluoroscopy images 1010, and therefore shows the path from the same angle 1090 at which the fluoroscopy images were acquired. As shown by the axes 1098, the pathway 1040 is two-dimensional. Stated differently, the 2D pathway 1040 describes the projection of the 3D path followed by the device onto the imaging plane at the imaging angle 1090.

As shown by the arrow 1062, because the two-dimensional path 1040 is generated based on the fluoroscopy images 1010, each position along the two-dimensional path 1040 may be associated with one or more fluoroscopy images 1010. As an example, at a location 1041 along the path 1040, the first fluoroscopy image 1010 may depict the intravascular device 1020 at that same position 1041. In addition, because a correspondence was also established between the fluoroscopy images 1010 and the intravascular data 1030 as shown by the arrow 1061, intravascular data 1030, such as the first IVUS image shown, may also be associated with the location 1041 along the path 1040 as shown by the arrow 1063.

Figure 9:
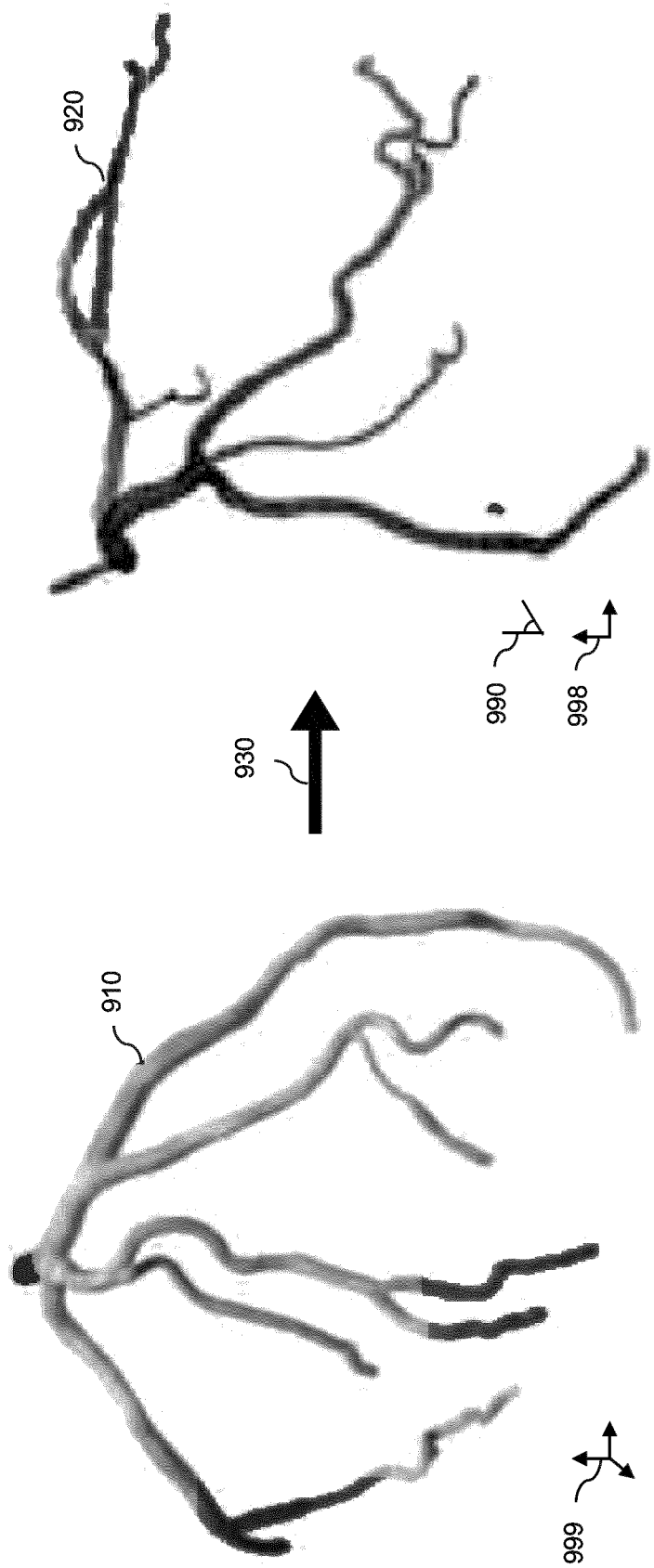
FIG. 9 is a diagrammatic view of a CT-based 3D model used to generate a CT-based 2D pathway, according to aspects of the disclosure.

At step 625, the method 600 includes generating multiple CT-based 2D pathways 920 by projecting the CT-based 3D model 910 at angles similar to the imaging angle 1090. Step 625 will be described with reference to FIG. 9 and FIG. 10. FIG. 9 is a diagrammatic view of a CT-based 3D model 910 used to generate a CT-based 2D pathway 920, according to aspects of the disclosure. In some embodiments, CT-based 2D pathways may additionally be referred to as a roadmap, a roadmap image, a path, or any other suitable term.

At step 625, the system 100 may extract a model 910 of the vascular tree from the CT model 800 of FIG. 8. Specifically, the CT model 800 of FIG. 8 shows the vessels 830 within and around the heart 820 as well as various other tissues, cavities, or other structures within and/or around the heart 820. The system 100 may use the model 800 to construct a new model 910 representing only the vessels 830 of the heart 820. In some embodiments, the step of extracting a model of the coronary tree may be performed after the patient examination or may be completed in post-processing. The CT-based model 910 may be a three-dimensional model as shown by the axes 999. The vessels 830 may include the region of the patient vasculature imaged by the intravascular device 1020 at step 615. Constructing a new 3D model 910 including only the vessels 830 of the heart 820 may be accomplished by any suitable method. For example, the system 100 may identify the vascular structures of the heart 820 using a multiscale coronary response (MSCAR) method. The system 100 may additionally or alternatively use segmentation algorithms, multiscale filtering methods, analysis of the eigen values of Hessian matrices, expectation-maximization (EM) estimation segmentation algorithms, artery tracking, or any other suitable method. The system 100 may additionally employ any suitable image processing or machine learning techniques, methods, feedback mechanisms, or algorithms to identify the coronary vascular tree within the CT model 800. In some embodiments, the method of identifying, segmenting, or extracting the vascular tree 910 from the CT model 800 may include some features similar to those described in the publication entitled, "AUTOMATED CORONARY ARTERY TREE EXTRACTION IN CORONARY CT ANGIOGRAPHY USING A MULTISCALE ENHANCEMENT AND DYNAMIC BALLOON TRACKING (MS-CAR-DBT) METHOD," Computerized Medical Imaging and Graphics, vol. 36, no. 1, pp. 1-10, January 2012, by C. Zhou et al. hereby incorporated by reference in its entirety.

As shown by the arrow 930, the CT-model 910 may be projected from three-dimensional space to two-dimensional space to create a CT-based 2D pathway 920 at an angle 990. The angle 990 may be any suitable angle. In some embodiments, the angle 990 may be the same as the imaging angle 1090 or the angle at which the fluoroscopy images 1010 were obtained. In some embodiments, the angle 990 may differ from the angle 1090 by one or more degrees as will be discussed in more detail hereafter. As shown by the axes 998, the CT-based pathway 920 is a two-dimensional image or model. The angle 990 may be referred to as a projection angle or source angle in some instances. It is noted that the pathway 920 is not an image directly acquired by an imaging device or system. Rather, it is a computer generated, two-dimensional projection of the 3D model. In some aspects, however, the CT-based 2D pathway 920 may resemble an angiography image received from an x-ray imaging device.

Any suitable method may be used by the system 100 to project the CT-based 3D model 910 to create the CT-based 2D pathway 920. For example, the CT-based 3D model may be received by the system 100. The CT-based 3D model 910 may include multiple three-dimensional coordinates corresponding to the locations of the coronary vessels 830 of the heart 820. In some embodiments, these three-dimensional coordinates may be organized into any suitable matrix, vector, set, series, or other means of data organization. The three-dimensional coordinates corresponding to the CT-based 3D model 910 may define centerlines along each vessel 830 shown in the model 910. The coordinates may also correspond to any other suitable location along the vessels 830. In an embodiment, the coordinates corresponding to the CT-based 3D model 910 may be combined into a matrix, M. A transformation matrix, K, may additionally be determined. The transformation matrix K may be any suitable matrix configured to transform or project the coordinates corresponding to the locations of the blood vessels 830 in three-dimensional space to a two-dimensional plane. For example, in an embodiment, the transformation matrix, K, may be a 3×3 matrix which may preserve the first and second values of a three-dimensional coordinate, while setting the third value to a constant. In some embodiments, the matrix K may additionally perform other matrix transformation functions, such as scaling, rotation, translation, reflection, skewing, shearing, or any other suitable transformation. The matrix K may additionally be correlated to the angle 990 at which the three-dimensional coordinates are projected onto a two-dimensional plane. In other embodiments, this angle may be applied separate from the matrix K. An equation may then be formed to project the three-dimensional coordinates of the CT-based 3D model 910 to a CT-based 2D pathway 920. The equation may be of any suitable form, include any suitable variables, constants, values, or coordinates, or may include one equation or a set of equations. In an embodiment, the equation used to project the three-dimensional coordinates of the CT-based 3D model 910 to the CT-based 2D pathway 920 may be similar to $A=KM$, in which A represents a matrix including two dimensional coordinates of a two-dimensional view of the vessels 820 shown at the projection angle 990. The two-dimensional nature of the CT-based 2D pathway 920 is additionally illustrated by the axes 998 of FIG. 9. It is additionally noted that the three-dimensional coordinates corresponding to the CT-based 3D model 910 and the two-dimensional coordinates corresponding to the CT-based 2D pathway 920 both shown in FIG. 9 may be of any suitable coordinate system, including a cartesian, rectangular, polar, cylindrical, spherical coordinate systems, or any other suitable coordinate systems.

At step 625, as stated, the method 600 includes creating multiple CT-based 2D pathways 920. These multiple CT-based pathways 920 may be created by varying the angle of projection 990 for each pathway 920. In this way, the two-dimensional pathways 920 may vary due to a difference in perspective between each pathway 920. For example, the configuration of vessels 830 shown each pathway 920 may be positioned at different locations within the two-dimensional plane. Stated differently, varying the projection angle 990 used to project the CT-based 3D model 910 to create a CT-based 2D pathway 920 may be a virtual equivalent of moving the x-ray source of an x-ray device to acquire a different x-ray image of a different perspective. In some embodiments, the projection angle 990 used to project the CT-based 3D model 910 to create a CT-based 2D pathway 920 may be any arbitrary angle and may be incrementally varied to create any suitable number of pathways 920 from different angles 990. For example, the pathways 920 may depict the vasculature from angles varying from one another by 1, 2, 3, or more degrees in each direction. The number of CT-based 2D pathways 920 created may therefore also vary. For example, the pathways 920 may include 1, 2, 3, 5, 10, 20, 50, 100, or more different pathways 920 or any suitable number therebetween, each created via a different projection angle 990. In some embodiments, the system 100 may create the set of CT-based 2D pathways 920 based on angles of projection 990 similar to the imaging angle 1090, or the angle of the x-ray source and detector when the fluoroscopy images 1010 were acquired. For example, the system 100 may generate one CT-based 2D pathway 920 at a projection angle 990 equal to the imaging angle 1090. The system may then vary the projection angle 990 by 5 degrees in a given direction, as an illustrative example and generate an additional CT-based 2D pathway 920 from the updated projection angle 990. The system 100 may determine ranges of projection angles 990 in any suitable direction at which a pathway 920 is created. For example, the system 100 may vary the projection angle 990 by a maximum of 15 degrees in each direction as opposed to generating pathways 920 from all directions to limit the number of CT-based 2D pathways 920 required.

Figure 11:
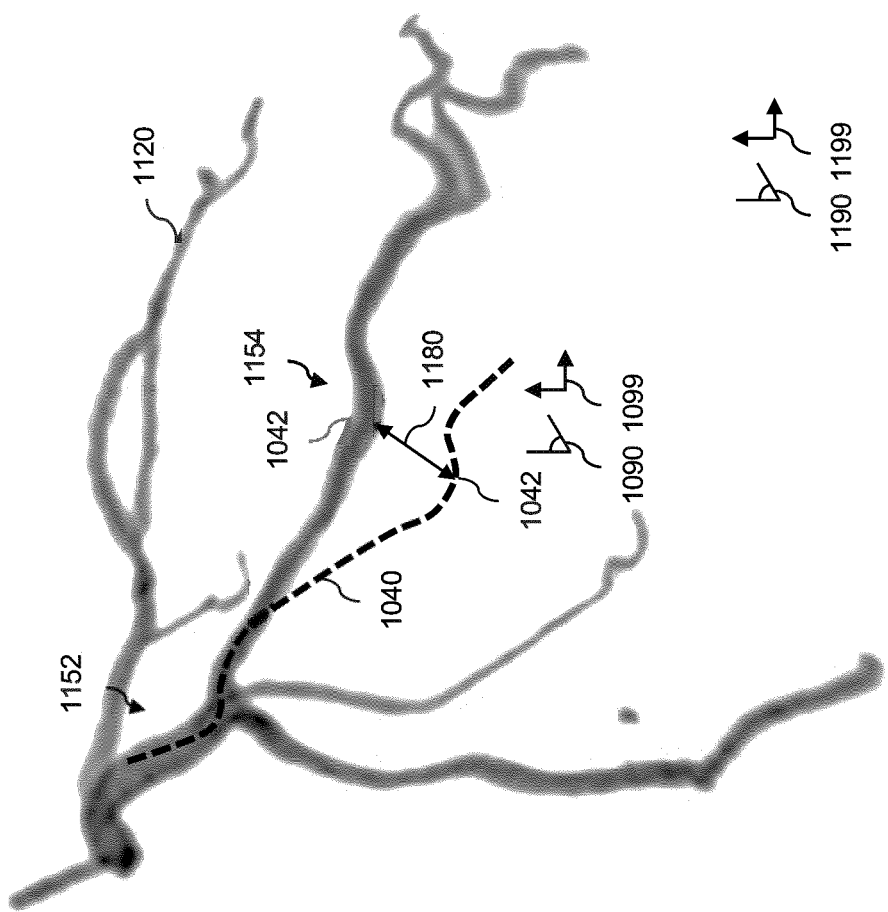
FIG. 11 is a diagrammatic view of the fluoroscopy-based 2D pathway overlaid on a CT-based 2D pathway, according to aspects of the present disclosure.

At step 630, the method 600 includes identifying a CT-based 2D pathway that is similar to the fluoroscopy-based 2D pathway 1040 of FIG. 10. Step 630 will be described with reference to FIG. 11 and FIG. 12. FIG. 11 is a diagrammatic view of the fluoroscopy-based 2D pathway 1040 overlaid on a CT-based 2D pathway 1120, according to aspects of the present disclosure.

Each generated pathway 920 in the set of CT-based 2D pathways 920 may be compared by the system 100 to the fluoroscopy-based 2D pathway 1040 created at step 620 and shown in FIG. 10. The system 100 may use any appropriate method, algorithm, or process to compare the CT-based 2D pathways 920 with the fluoroscopy-based 2D pathway 1040. For example, the system 100 may employ any suitable image processing techniques or machine learning techniques listed herein.

In the example shown in FIG. 11, the fluoroscopy-based 2D pathway 1040 may be overlaid over a CT-based 2D pathway 1120. The CT-based 2D pathway 1120 shown in FIG. 11 may be one of the set of CT-based 2D pathways 920 generated by the system 100 at step 625. As shown in FIG. 11, the fluoroscopy-based 2D pathway 1040 may be acquired at the angle 1090 and may be a two-dimensional depiction, as shown by the axes 1099. Similarly, the CT-based 2D pathway 1120 may be a two-dimensional depiction as shown by the axes 1199. The CT-based 2D pathway 1120 may be created by projecting the CT-based 3D model 910 onto a two-dimensional plane using any of the previously mentioned equations or techniques at an angle 1190. In some embodiments, the projection angle 1190 may be the same angle as the imaging angle 1090. The projection angle 1190 may also differ from the imaging angle 1090. As shown in FIG. 11, the position and shape of the fluoroscopy-based 2D pathway 1040 does not correlate to the position and shape of any of the vessels of the CT-based 2D pathway 1120. In some embodiments, although the projection angle 1190 may be the same as the imaging angle 1090, the CT-based 2D pathway 1120 may not align with the fluoroscopy-based 2D pathway due to differences in the positioning of the patient anatomy during the CT imaging procedure and the fluoroscopy and intravascular procedure. For example, at a region 1152 of the imaged vessel, the pathway 1040 and the pathway 1120 may be similar. In other embodiments, portions of the pathway 1040 and the pathway 1120 may also correspond to one another. However, at a region 1154, the fluoroscopy-based pathway 1040 and the CT-based pathway 1120 diverge. Specifically, at a point 1042 identified along the fluoroscopy-based pathway 1040 and identified along a potentially corresponding vessel within the CT-based pathway 1120, a separation 1180 is observed. In some embodiments, this separation 1180 may be quantified and stored in a memory corresponding to the CT-based pathway 1120 and/or the point 1042. Additional separations between the fluoroscopy-based pathway 1040 and the CT-based pathway 1120 are also shown in and around the region 1154 in FIG. 11. In some embodiments, the system 100 may generate an overlap score or other metric relating to the similarity of the pathway 1040 and the pathway 1120. This overlap score may then be incorporated in a feedback mechanism to select the pathway 1040 relating to the projection angle that is most similar to the pathway 1120. The feedback mechanism may be or include any suitable image processing techniques and/or machine learning techniques or networks, as will be described in more detail hereafter.

Figure 12:
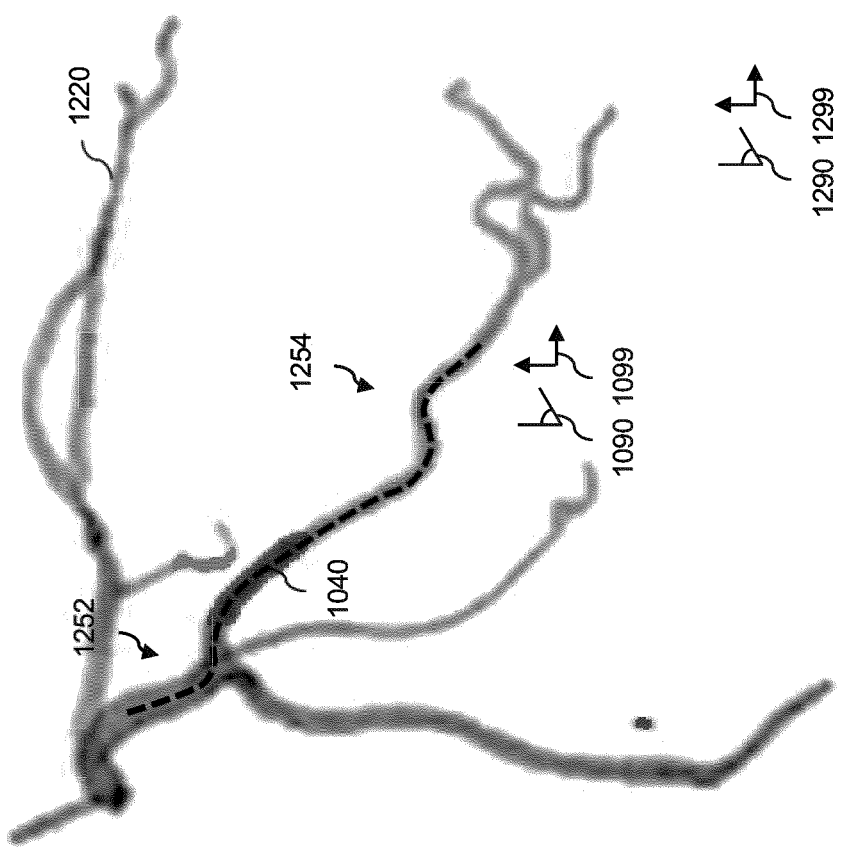
FIG. 12 is a diagrammatic view of the fluoroscopy-based 2D pathway overlaid on a CT-based 2D pathway, according to aspects of the present disclosure.

FIG. 12 is a diagrammatic view of the fluoroscopy-based 2D pathway 1040 overlaid on a different CT-based 2D pathway 1220, according to aspects of the present disclosure. Similar to FIG. 11, the fluoroscopy-based 2D pathway 1040 may be overlaid over a CT-based 2D pathway 1220. The pathway 1220 may also be one of the set of CT-based 2D pathways 920 previously discussed. The CT-based 2D pathway 1220 shown in FIG. 12 may differ from the pathway 1120 of FIG. 11 in that it may be generated by projecting the CT-based model 910 at a different angle 1290. As shown by the axes 1299, the CT-based 2D pathway 1220 is two-dimensional. In some embodiments, the projection angle 1290 may be the same angle as the imaging angle 1090. The projection angle 1290 may also differ from the imaging angle 1090. As shown in FIG. 12, the position and shape of the fluoroscopy-based 2D pathway 1040 correlates to the position and shape of one of the vessels of the CT-based 2D pathway 1220. For example, at a region 1252 of the imaged vessel, the pathway 1040 and the pathway 1120 are similar or comparable in shape, position, and curvature. Stated differently, the positions of two-dimensional coordinates defining the fluoroscopy-based 2D pathway 1040 are the same or substantially similar to the centerline of the vessels shown in the CT-based 2D pathway 1220. As shown in FIG. 12, the correlation of position, shape, and curvature of the fluoroscopy-based pathway 1040 and the CT-based pathway 1220 is maintained at all locations along the fluoroscopy-based 2D pathway 1040. That is, at a region 1254 distal of the region 1252, the fluoroscopy-based pathway 1040 and the CT-based pathway 1220 still correlate to one another such that there is no significant distance or separation between the two pathways 1040 and 1220 at any position.

In some embodiments, the system 100 may compare the fluoroscopy-based 2D pathway 1040 with each CT-based 2D pathway 920 in a similar manner as shown in FIGS. 11 and 12. In some embodiments, the system may identify multiple points along the fluoroscopy-based pathway 1040 and corresponding points along the corresponding vessel in the CT-based pathway 920, including either of the pathways 1120 and 1220 shown in FIGS. 11 and 12. Points may be identified by the system 100 or by a user of the system 100. In embodiments in which points along the pathways 1040 and 920 are identified by the system 100, the system 100 may identified by any suitable method. For example, the system 100 may identify locations along the pathways 1040 and 920 may use such techniques as a global shift algorithm, warping algorithm, path solving algorithm, calibration algorithm, motion compensation algorithm, modified mean shift algorithm, or any other suitable algorithm, technique, or method. The system 100 may also use any suitable machine learning techniques to identify corresponding positions along the pathways 1040 and 920. For example, the machine learning techniques may include a deep learning network which employs processing algorithms such as convolutional layers, fully convolutional layers, fully connected layers, feature vectors, or other algorithms or techniques. In some embodiments, a deep learning network may be trained to identify anatomical landmarks along the pathways 1040 and 920 based on trained classification outputs and associated confidence scores. These landmarks may then be used to identify multiple points along the pathways 1040 and 920. It is noted that any of the described feedback mechanisms, image processing techniques, and/or machine learning techniques may be used by the system 100 to identify locations along the pathways 1040 and 920 as discussed, but also the pathways 1120 and 1220 as well as any locations along the vessels of the CT-based 3D model 910 and/or the model 800 previously discussed.

In some embodiments, after various points are identified along the pathways 1040 and 920, the system may calculate a metrics corresponding to differences in position between points along the pathway 1040 and corresponding points along the pathway 920 being compared. These points may be substantially similar to the point 1042 shown in FIG. 11 but may be at any suitable location along the pathways 1040 and 920. The points may correspond to anatomical landmarks identified in the pathways 1040 and 920 or may correspond to any other suitable locations. The metrics corresponding to differences in positions of points along the pathways 1040 and 920 may be substantially similar to the separation 1180 shown in FIG. 11. In some embodiments, the system 100 may store these metrics when comparing the fluoroscopy-based 2D pathway 1040 to various CT-based 2D pathways 920.

In some embodiments, the system 100 may overlay the fluoroscopy-based 2D pathway 1040 over all vessels shown in each CT-based 2D pathway 920. In other embodiments, using any of the previously identified feedback mechanisms, image processing techniques, or machine learning techniques previously discussed, the system 100 may identify one vessel that most closely corresponds to the fluoroscopy-based pathway 1040 and perform a comparison of the pathway 1040 with the selected vessel. In some embodiments, any other suitable methods of shape comparison or differentiation may be used to compare the pathways 1040 and 920. For example, the system 100 may employ an area overlap technique, may compare the curvature or tortuosity of regions of the vasculature, may compare lengths of the vessels in the vasculature, may compare occlusions, bifurcations, or any other anatomical landmarks within the vasculature, or may use any other suitable method. In some embodiments, the system 100 may account for scaling, rotation, translation, or other characteristics when comparing the pathways 1040 and 920.

As stated in step 630, the system 100 may identify a pathway 920 that is similar or comparable to the fluoroscopy-based 2D pathway 1040. In some embodiments, the system 100 or a user of the system 100 may determine a threshold value corresponding to the stored metrics of separation between points along the pathways 1040 and 920. In some embodiments, the separation between points along the pathways 1040 and 920 may be added, averaged, multiplied or otherwise combined to create a similarity measure corresponding to the comparison between the pathways 1040 and 920. The similarity measure may also be referred to as a similarity index. The similarity measure may be determined via any suitable method or may be of any suitable type. For example, the similarity measure may be based on distances between points along both pathways 1040 and 920 as stated. The similarity measure may also be based on the curvature or tortuosity of regions of vessels within the pathways 1040 and 920, the lengths of vessels within the pathways, locations of occlusions of the vessels within the pathways, locations of bifurcations within the vessels, or any other anatomical landmarks within the vessels shown in the pathways 1040 and 920. In an embodiment, in order for a CT-based 2D pathway 920 to be sufficiently similar to the fluoroscopy-based pathway 1040, this combined similarity measure must satisfy (e.g., greater than, less than, equal to) a predetermined threshold value. In another embodiment, in order for a CT-based 2D pathway 920 to be sufficiently similar to the fluoroscopy-based pathway 1040, each metric of separation between corresponding points along the pathways 1040 and 920 must satisfy (e.g., greater than, less than, equal to) the predetermined threshold. In some embodiments, the CT-based 2D pathway 920 which shows the least differences between corresponding points along pathways 1040 and 920 or the smallest metrics of separation may be selected by the system 100 at step 630. The system 100 may use any other suitable method of comparing the pathways 1040 and 920. For example, the system 100 may use any of the previously mentioned feedback mechanisms, image processing techniques, or machine learning techniques or other methods of shape analysis. In an embodiment, the CT-based 2D pathway 920 selected by the system 100 at step 630 may be the CT-based 2D pathway 1220 shown in FIG. 12.

In an embodiment in which machine learning techniques are employed to compare the pathways 920 with the fluoroscopy-based 2D pathway and select a pathway 920, aspects of the disclosure may include a deep learning network (e.g., a convolutional neural network, a multi-class classification network, an encoder-decoder type network, or any suitable network). The deep learning network configuration may be trained for identification of the pathway 920 that is most similar to the fluoroscopy-based 2D pathway 1040. The deep learning network configuration may be or include a feedback mechanism. In some embodiments, the feedback mechanism may indicate a confidence score relating to the similarity of a pathway 920 with the pathway 1040. Based on the output of the feedback mechanism, the network configuration may search the input pathways 920 to identify a pathway 920 which is most similar to the fluoroscopy-based 2D pathway 1040. In this way, any suitable machine learning techniques may be used by the system 100 at any step of any method to direct the search and comparison of pathways or other data through a feedback mechanism.

At step 635, the method 600 includes co-registering the intravascular data 1030 and the CT-based 2D pathway 1220 identified in step 630 by mapping the locations of the fluoroscopy-based 2D pathway 1040 and the CT-based 2D pathway 1220. The step 635 will be described with reference to FIG. 10.

At step 635, the system 100 or a user of the system 100 may associate any suitable anatomical features identified in the fluoroscopy-based pathway 1040 with the same anatomical features in the CT-based 2D pathway 1220 to create a mapping between the two pathways. In some embodiments, the system 100 or a user of the system 100 may identify anatomical features in the fluoroscopy pathway 1040 and in each CT-based pathway 920 prior to comparison of the various pathways or calculation of any metrics relating to the pathways 1040 and/or 920 as described in step 630. The anatomical features identified may be any suitable features. For example, the anatomical features may include, but are not limited to, occlusions or regions of constrictions of a vessel, tortuosity of a vessel, bifurcations, or lengths of a vessel, among other features. This association of anatomical features in the fluoroscopy-based 2D pathway 1040 and the CT-based 2D pathway 1220 creates a mapping of physical positions or locations along the vasculature on both pathways or models.

In an embodiment in which the system 100 identifies the previously listed anatomical landmarks, the system 100 may identify anatomical landmarks via any suitable method. For example, the system 100 may employ image processing techniques such as any of the previously mentioned algorithms, techniques, or methods. In addition, the system 100 may segment received images or models or perform various other steps to identify anatomical features. In other embodiments, the system 100 may employ artificial intelligence techniques such as a deep learning network to identify anatomical features including any of the previously listed machine learning techniques, algorithms, or methods.

The feature mapping of locations within the vessel defined by the fluoroscopy-based 2D pathway 1040 and the CT-based 2D pathway 1220 may be configured to allow a user to correlate any location along a vessel shown in either pathway to the other model. To achieve this comprehensive one-to-one feature mapping between the pathways, the mapping correspondences between identified anatomical landmarks may be expanded or extrapolated to include the entire pathway 1040 and pathway 1220. In such a configuration, any location, including locations not associated with an identified landmark, on the fluoroscopy-based pathway 1040 may be identified or otherwise associated with the same location on the CT-based pathway 1220 and vice versa. The system 100 may employ any suitable method or technique to achieve this comprehensive correspondence between all points along the fluoroscopy-based 2D pathway 1040 and the CT-based 2D pathway 1220.

Referring to FIG. 10, in some embodiments, an anatomical landmark or feature may be identified in both the fluoroscopy-based pathway 1040 and the CT-based pathway 1220. In the example shown in FIG. 10, the pathway 1040 is compared with the pathway 920, but it is understood that any description of comparing the pathway 1040 with the pathway 920 may equally apply to comparisons with the pathways 1120 and/or 1220. As an example, an identified landmark or features may correspond to the point 1041 shown along the vessel in both the fluoroscopy-based 2D pathway 1040 and the CT-based 2D pathway 920 shown in FIG. 10. The system 100 may establish a mapping correspondence between the identified landmark or feature shown by the point 1041 in the pathway 1040 and the same landmark or feature shown by the point 1041 in the pathway 1220. This mapping correspondence may indicate that position data, or other data including intravascular data, associated with the point 1041 in the pathway 1040 may be associated and presented with the same point 1041 on the pathway 920 and vice versa. The system 100 may additionally establish a correspondence between locations near the identified anatomical landmark or feature shown by the point 1041. In an embodiment, a point may be selected in a region along the vessel proximal to the point 1041 along the pathway 1040. The system 100 may calculate, via any of the previously mentioned image processing or artificial intelligence techniques, the distance between the selected proximal point and the point 1041. The system may then identify the same proximal point in the CT-based pathway 920 based on this determined distance. In some embodiments, the system 100 may additionally determine an angle or vector corresponding to the difference in positions between the proximal point and the point 1041. Once the proximal point has been identified in both the pathways 1040 and 920, a mapping correspondence or relationship. The system 100 may apply this same technique to identify any locations proximal or distal to the position of an anatomical landmark or feature similar to that shown by the point 1041. In this way, the system 100 may establish a one-to-one correlation between any location or position along the fluoroscopy-based 2D pathway 1040 and the CT-based 2D pathway 920. This mapping correspondence between all locations along the pathway 1040 and the pathway 920 is shown by the arrow 1064 in FIG. 10.

After a mapping between corresponding locations along the fluoroscopy-based 2D pathway 1040 and the CT-based 2D pathway 920 has been established, the intravascular data 1030 may be co-registered to the CT-based 2D pathway 920. This co-registration may be represented both by the arrow 1064 and the arrow 1065 shown in FIG. 10. Specifically, the intravascular data 1030 may be associated with the pathway 920 as shown by the arrow 1065 and the location data corresponding to the intravascular data 1030 may be associated with the pathway 920 as shown by the arrow 1064. In this way, just as different fluoroscopy images 1010 and intravascular data 1030 may be associated with various locations along the fluoroscopy-based 2D pathway 1040, the fluoroscopy images 1010 and intravascular data 1030 may be associated with the same locations along the CT-based 2D pathway 920. For example, the same location 1041 may be identified on the CT-based 2D pathway 920 using any of the techniques previously described. The same fluoroscopy images 1010 associated with the location 1041 on the fluoroscopy-based pathway 1040 may be associated with the same location 1041 on the CT-based 2D pathway 920. Similarly, the same intravascular data 1030 associated with the location 1041 on the fluoroscopy-based pathway 1040 may also be associated with the same location 1041 on the CT-based 2D pathway 920.

At step 640, the method 600 includes co-registering the intravascular data 1030 with the CT-based 3D model 910 based on the mapping established at step 635. The step 640 will also be described with reference to FIG. 10. To co-register the intravascular data 1030 obtained to the CT-based 3D model 910, the CT-based 2D pathway 920 may be projected back to the CT-based 3D model 910 such that all the intravascular data 1030, fluoroscopy data 1010, or any other suitable data co-registered to the CT-based 2D pathway 920 may be similarly co-registered to the CT-based 3D model 910. For example, the location information corresponding to any received data may be received, or a correspondence between the same locations may be established, as shown by the arrow 1067. Similarly, the intravascular data 1030 or any other data may be co-registered with the CT-based 3D model 910 as shown by the arrow 1066. This projection of the CT-based 2D pathway may be performed by calculating an inverse of the transformation matrices and/or equations previously discussed with reference to FIG. 9. For example, the projection angle 990 pertaining to the selected CT-based 2D pathway 920 may be stored by the system 100 within a memory. This projection angle 990 may be used to project the CT-based 2D pathway 920 to the CT-based 3D model 910 using any of the previously discussed methods or techniques. As shown by the axes 999, the CT-based model 910 is three-dimensional.

Figure 13:
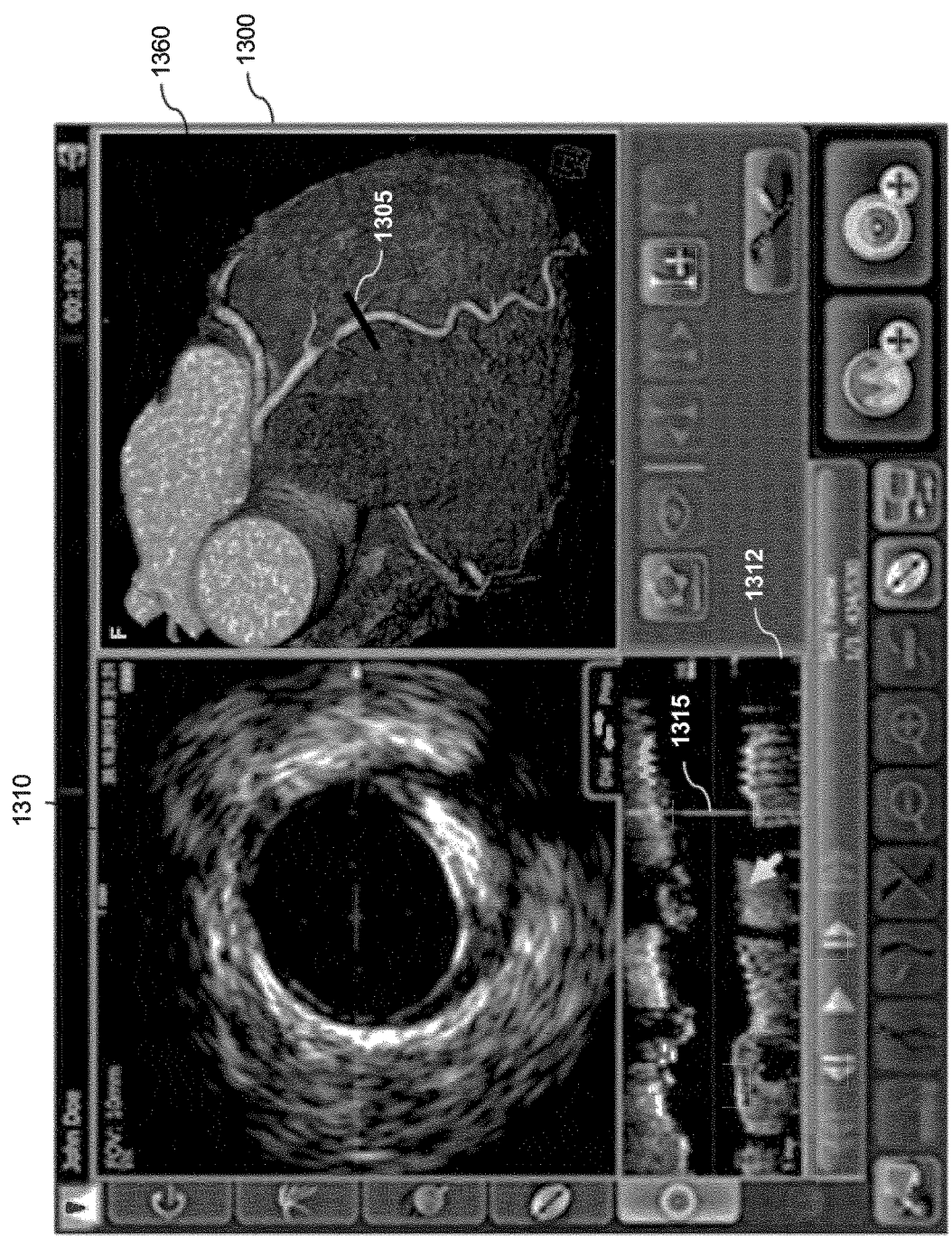
FIG. 13 is a diagrammatic view of a graphical user interface displaying intravascular data co-registered to a CT-based 3D model, according to aspects of the present disclosure.

At step 645, the method 600 includes outputting to a display a CT-based 3D model 1360 and a graphical representation of the intravascular data 1310. Step 645 will be described with reference to FIGS. 13 and 14. FIG. 13 is a diagrammatic view of a graphical user interface 1400 displaying intravascular data 1310 coregistered to the CT-based 3D model 700, according to aspects of the present disclosure. FIG. 13 additionally depicts an indicator 1315, an image longitudinal display (ILD) 1312, and an indicator 1305.

The CT-based model 1360 output to a display may be either the CT-based 3D model 910 shown in FIGS. 9 and 10 or may be the CT-based 3D model 800 shown in FIG. 8. The co-registered intravascular data 1310 may include the intravascular data 1030 presented in FIG. 10 or any other data. The CT-based model 1360 with co-registered intravascular data 1310 may be displayed to a user in any suitable format. For example, as shown in FIG. 13, the CT-based model 1360 may be displayed adjacent to the corresponding intravascular data 1310. The intravascular data 1310 may be an IVUS image. In other embodiments, co-registered intravascular data 1310 may include any other suitable images, metrics, or other data and may be overlaid over the CT-based model 1360 or arranged or displayed in any other suitable configuration.

In the embodiment shown in FIG. 13, the indicator 1305 is positioned over the CT-based three-dimensional model 1360 at a location along a vessel imaged by the intravascular device 1020 (FIG. 10). The IVUS image 1310 displayed adjacent to the CT-based model 1360 is an image acquired by the intravascular device at the location identified by the indicator 1305. For example, the location identified by the indicator 1305 may correspond to the location 1041 previously identified in FIG. 10. The fluoroscopy image 1010 and IVUS image 1030 shown in FIG. 10 may be associated with the location 1041 fluoroscopy-based 2D pathway 1040 and/or the CT-based 2D pathway 920 in FIG. 10. This same location 1041 and its associated IVUS image(s) and/or fluoroscopy image(s) may then be co-registered to the CT-based model 1360 as previously described. This allows the IVUS image obtained at the location 1041 to be displayed alongside the three-dimensional CT-based model 1360 indicating the co-registered location 1041 at which the IVUS image was obtained via the indicator 1305. In some embodiments, a user of the system 100 may also select an additional IVUS image to be displayed in the graphical user interface 1300. As a different IVUS image is selected, the indicator 1305 would move to a different location along the vessel corresponding to the location at which the selected IVUS image was obtained. In some embodiments, a user of the system 100 may additionally move the indicator 1305 along any vessel shown in the CT-based model 1360 and an IVUS image corresponding to the selected location would be displayed to the user if an IVUS image is available.

In some embodiments, additional images may be included and displayed to a user of the system 100, including the image longitudinal display (ILD) 1312. The ILD 1312 may provide the user with a longitudinal view of the vessel imaged with the intravascular device. Specifically, one end of the ILD 1312 may correspond to the proximal most region of the imaged vessel and the opposing end of the ILD 1312 may correspond to the distal most region of the imaged vessel. The ILD 1312 may provide a graphical representation of relative diameters of the imaged vessel at all positions along the imaged vessel. The ILD 1312 may include an indicator 1315. The indicator 1315 may correspond to the position of the intravascular device relative to the entire imaged vessel at the location at which the displayed IVUS image was obtained. In this way, as the indicator 1305 is moved by a user to a different location along the vessel, a different IVUS image would be displayed adjacent to the CT-based model 1360 and the indicator 1315 would also move to a different corresponding position within the ILD 1312. In some embodiments, a user may be able to move the indicator 1315 to a different location within the ILD 1312 as well and cause the system 100 to recall and display an associated IVUS image as well as move the indicator 1305 to a different corresponding position within the CT-based model 1360.

The system 100 may display additional images or metrics to a user. For example, the system 100 may display any of the previously discussed images such as the fluoroscopy images 1010, the fluoroscopy-based 2D pathway 1040, any CT-based 2D pathway 920, 1120, and/or 1220, or the CT-based 3D model 910. The system 100 may additionally display any suitable indicators or metrics associated with any of these images.

Figure 14:
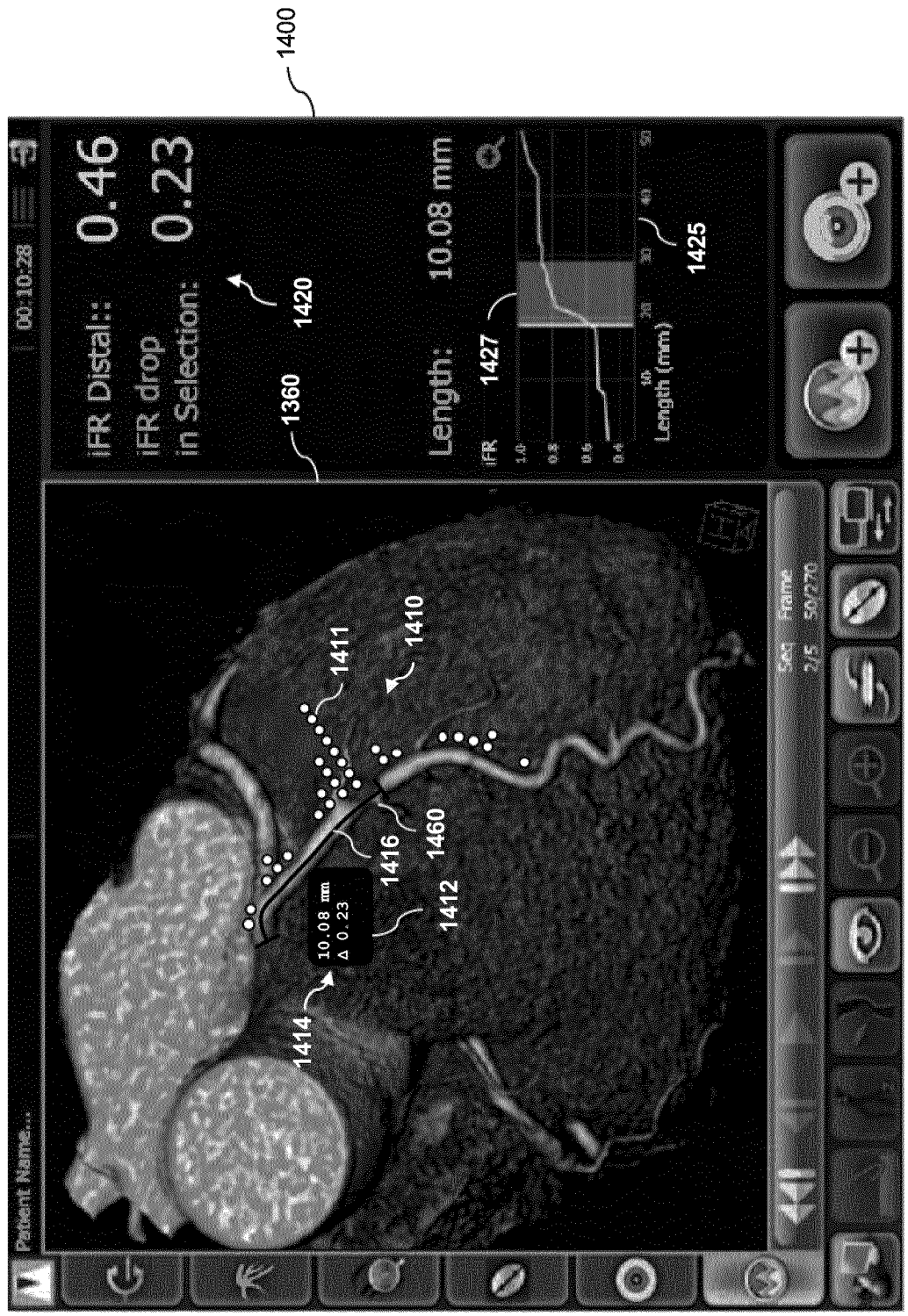
FIG. 14 is a diagrammatic view of a graphical user interface displaying intravascular data co-registered to a CT-based 3D model, according to aspects of the present disclosure.

FIG. 14 is a diagrammatic view of a graphical user interface 1400 displaying intravascular data 1410 co-registered to the CT-based 3D model 1360, according to aspects of the present disclosure. In the example graphical user interface 1400 shown in FIG. 14, the intravascular data 1410 may correspond to intravascular data other than IVUS data. For example, the intravascular 1410 may correspond to iFR data, but in other embodiments, the intravascular data may alternatively correspond to FFR data, OCT data, or any other suitable intravascular data. The intravascular data 1410 includes pressure difference indicators 1411, an indicator 1416, pressure metrics 1420, a graph 1425, a region 1427, a graphical element 1412, and metrics 1414.

As shown in FIG. 14, graphical representations corresponding to intravascular data 1410 may be overlaid over the CT-based model 1360. In other embodiments, intravascular data 1410 may be displayed adjacent to the CT-based model 1360 or in any other configuration. In the embodiment shown in FIG. 14, the intravascular data 1410 includes multiple pressure difference indicators 1411. The pressure difference indicators 1411 may convey to a user the severity of differences in pressure at various locations along the measured vessel. The number of indicators 1411 may correspond to the severity of pressure difference. For instance, near an occlusion 1460, the difference in pressure may be the most significant. The greatest number of indicators 1411 may then be positioned by the location of the occlusion 1460. In the embodiment shown, the indicators 1411 may be positioned extending in a straight line perpendicular to the vessel. However, the pressure difference indicators 1411 may be arranged in any suitable manner. For example, they may not extend in a straight line, but may extend in any angled or curvilinear line. The indicators 1411 may also be arranged according to any suitable arrangement or pattern which may convey to a user any suitable metric associated with the vessel at a particular location. Although the pressure difference indicators 1411 are of a circular shape in FIG. 14, the indicators 1411 may be of any suitable type. For example, they may be of any suitable geometric or non-geometric shape or size or may be or include any suitable alphanumeric characters.

The graph 1425 adjacent to the CT-based model 1360 may indicate intravascular pressure at all locations along the measured length of the vessel. For example, an x-axis of the graph 1425 may indicate the distance of locations along the vessel from the most distal or most proximal position within the vessel at which intravascular measurements were obtained. A y-axis of the graph 1425 may indicate the quantity of intravascular measurement, in this case, iFR measurement data. In some embodiments, a user of the system 100 may select a region 1427 within the graph 1425. The region 1427 corresponds to a length of the measured vessel. The region 1427 may additionally correspond to the indicator 1416 overlaid on the CT-based model 1360. The indicator 1416 illustrates the same selected length of vessel on the CT-based model 1360. In some embodiments, the selected length may be selected by the user either on the CT-based model 1360 or on the graph 1425.

Upon selection of a region 1427 and/or length shown by the indicator 1416, the system 100 may generate and display one or more metrics associated with the selected length of vessel. For example, the metrics 1420 may include metrics such as iFR or other measurements relating to a drop or change in pressure across the selected region 1427. Any additional metrics may also be displayed, such as pressure data related to the distal most location within the selected region 1427, the proximal most location, an average pressure metric, or any other suitable metrics. The metrics 1420 may additionally include pressure or other intravascular data related to the measured vessel such as an iFR measurement at the distal most measured position of the vessel. The metrics 1420 may additionally include any other suitable intravascular data metrics, such as average pressure or iFR measurements along the entire measured portion of the vessel, change in pressure or iFR measurements along the entire measured portion of the vessel, or any other suitable metrics. The metrics 1420 may be displayed in any suitable location within the graphical user interface, including overlaid on the CT-based model 1360, adjacent to or near the CT-based model 1360, overlaid on the graph 1425, or adjacent to or near the graph 1425, or at any other position suitable and in any other suitable arrangement, orientation, or organization.

Upon selection of a region 1427 and/or length shown by the indicator 1416, the system 100 may also generate the graphical element 1412. The graphical element 1412 may display the same, similar, or different metrics associated with the selected region 1427. The metrics 1414 shown within the graphical element 1412 may indicate the length of the selected region 1427 and the change or drop in pressure or iFR measurements along the selected region 1427. The metrics 1414 may additionally or alternatively include any other suitable metrics including any of those listed with reference to metrics 1420. Similar to the metrics 1420, the metrics 1414 may be displayed in any suitable location within the graphical user interface, including overlaid on the CT-based model 1360, adjacent to or near the CT-based model 1360, overlaid on the graph 1425, or adjacent to or near the graph 1425, or at any other suitable position and in any other suitable arrangement, orientation, or organization. It is noted that the method 600 described herein, as well as other similar methods described, allow coregistration of 3D models with 2D projections even when the angle of acquired two-dimensional images is not obvious or known providing for increased flexibility to users of the system.

Figure 7:
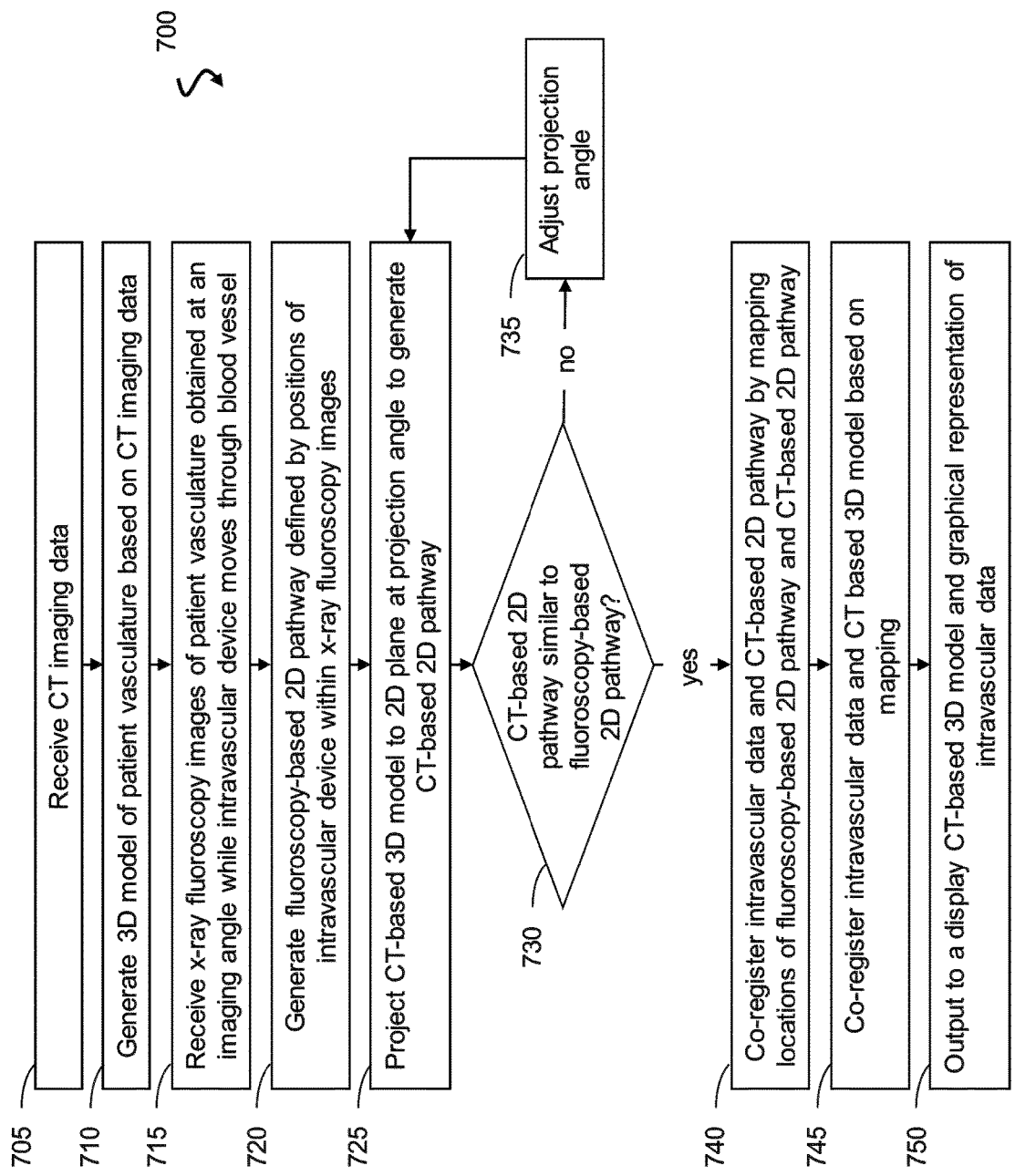
FIG. 7 is a flow diagram of a method of co-registering intravascular data with a CT-based 3D model, according to aspects of the present disclosure.

FIG. 7 is a flow diagram of a method 700 of co-registering intravascular data with a CT-based 3D model, according to aspects of the present disclosure. As illustrated, the method 700 includes a number of enumerated steps, but embodiments of the method 700 may include additional steps before, after, or in between the enumerated steps. In some embodiments, one or more of the enumerated steps may be omitted, performed in a different order, or performed concurrently. The steps of the method 700 can be carried out by any suitable component within the diagnostic system 100 and all steps need not be carried out by the same component. In some embodiments, one or more steps of the method 700 can be performed by, or at the direction of, a processor circuit of the diagnostic system 100, including, e.g., the processor 560 (FIG. 5) or any other component.

The method 700 is an additional embodiment of the present disclosure. Various steps of the method 700 may be substantially similar to steps of the method 600 previously described. Specifically, the steps 705-720 of the method 700 are the same as the steps 605-620 of the method 600. No specific description will be given with reference to steps 705-720 because the description of steps 705-720 is the same as the description of the steps 605-620.

Step 725 of the method 700 includes projecting the CT-based 3D model 910 to a 2D plane at a projection angle 990 to generate a CT-based 2D pathway 920. Step 725 will be described with reference to FIG. 9. In some aspects, the step 725 may be similar to the step 625 of the method 600. In particular, the model 910 may be projected to a 2D plane at the projection angle 990 using any of the previously mentioned transformation matrices or may involve any of the previously mentioned image processing or machine learning techniques previously described.

Step 725 of the method 700 differs from step 625 of the method 600 in that only one CT-based 2D pathway 920 is created at the step 725. In some embodiments and the first time the step 725 of the method 700 is performed by a processor of the system 100, the projection angle 990 may equal the imaging angle 1090.

Step 730 of the method 700 includes comparing the CT-based 2D pathway 920 generated at step 725 to the fluoroscopy-based 2D pathway 1040. This comparison may be accomplished via any of the previously described methods or techniques with reference to FIGS. 11 and 12. As previously described with reference to step 630 of the method 600, in some embodiments, the distance between corresponding points along the fluoroscopy-based 2D pathway 1040 and the CT-based 2D pathway 920 may be calculated by the system 100 and compared to a threshold value. In other embodiments, an overlap measure may be determined and compared to a threshold value. In some embodiments, any of the same comparison techniques previously identified may be used together to form a similarity measure or similarity index. If the similarity index is determined to be within the maximum threshold determined by the system 100 or a user of the system 100, the CT-based 2D pathway 920 may be selected by the system 100 and the method proceeds to step 740 as illustrated. If however, the system 100 determines that the distance between corresponding points on the pathways 1040 and 920 exceed the predetermined threshold, the system may determine that the pathways 1040 and 920 are not sufficiently similar to successfully perform a co-registration of the data. If this is the case, the system may proceed to step 735.

Step 735 of the method includes adjusting the projection angle 990. The projection angle 990 may be adjusted to any suitable angle. In some embodiments, the projection angle 990 may be adjusted by a small increment. For example, the projection angle 990 may be varied by ±1, 2, 3, 5, 10, 15 or more degrees, or by any other suitable change of angle, in any suitable direction.

After the projection angle 990 is adjusted, the system may revert back to step 725 and the CT-based 3D model 910 may be projected to form an additional CT-based 2D pathway 920 at the new projection angle 990. At step 730, the system 100 may once again compare the newly generated CT-based 2D pathway 920 with the fluoroscopy-based 2D pathway 1040 and determine whether the two pathways 1040 and 920 are sufficiently similar to proceed to co-registration at step 740. If the differences between the pathway 1040 and the newly created pathway 920 still exceed the predetermined threshold value, the system may again revert to step 735 and adjust the projection angle 990 again. In some embodiments, the projection angle 990 may be varied by the same amount as the projection angle 990 was adjusted at step 735 as previously described. In some embodiments, the projection angle may be adjusted by the same increment each time the system 100 performs step 735. In other embodiments, the system 100 may vary the amount by which the projection angle 990 is adjusted each time the system performs step 735. In some embodiments, the amount and direction of variation of the projection angle 990 may be determined by an output of any of the previously mentioned comparison techniques described with reference to step 730.

In some embodiments, the system 100 will sequentially perform and repeat steps 725, 730, and step 735 until the differences between the fluoroscopy-based 2D pathway 1040 and the CT-based 2D pathway 920 are less than a predetermined threshold, at which point the system 100 may proceed to step 740.

A shown in FIG. 7, the steps 740-750 of the method 700 are the same as the steps 635-645 of the method 600.

Figure 15:
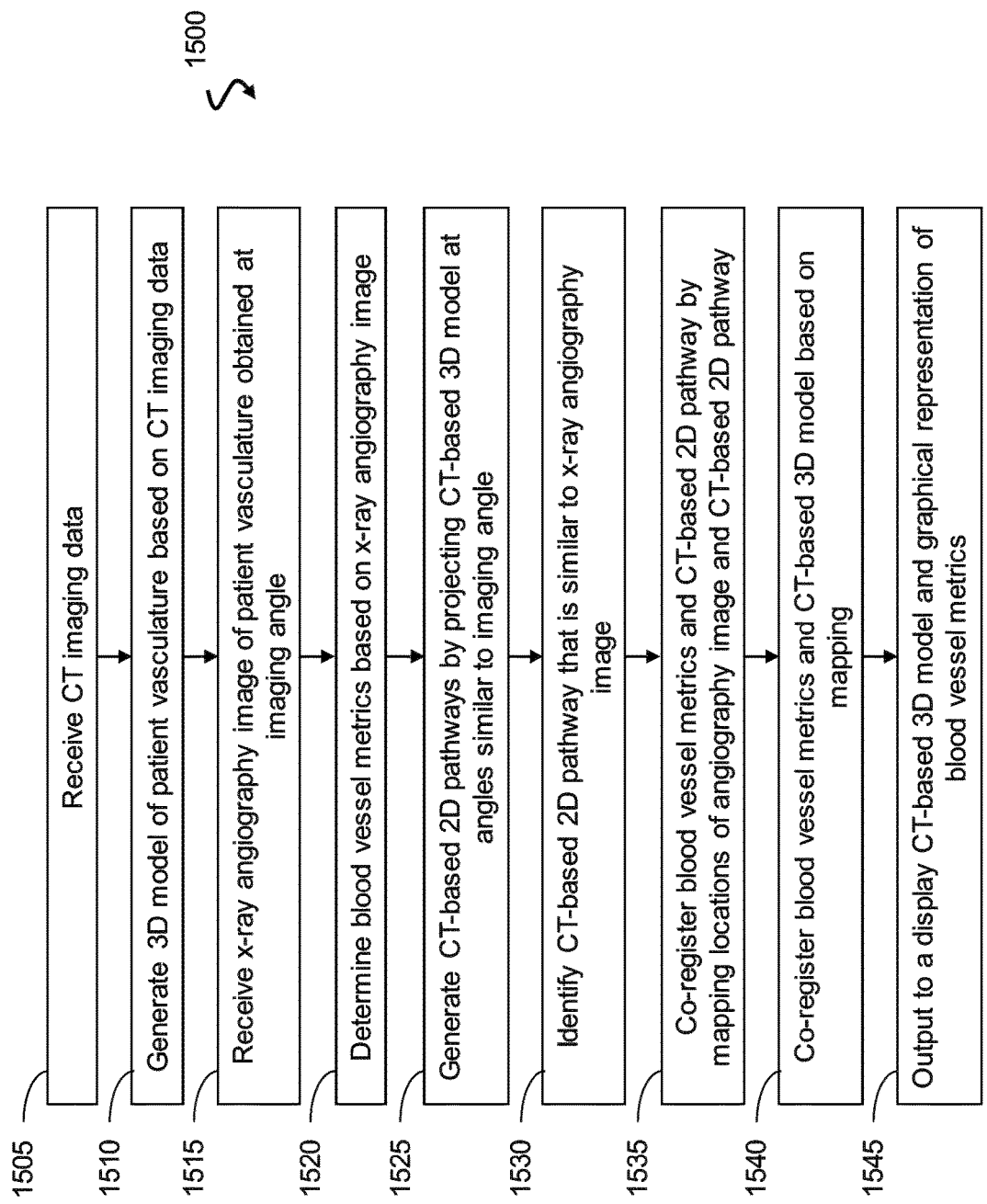
FIG. 15 is a flow diagram of a method of co-registering angiography-based data with a CT-based 3D model, according to aspects of the present disclosure.

FIG. 15 is a flow diagram of a method 1500 of co-registering angiography-based data with a CT-based 3D model, according to aspects of the present disclosure. One or more steps of the method 1500 will be described with reference to FIGS. 17-20. As illustrated, the method 1500 includes a number of enumerated steps, but embodiments of the method 1500 may include additional steps before, after, or in between the enumerated steps. In some embodiments, one or more of the enumerated steps may be omitted, performed in a different order, or performed concurrently. The steps of the method 1500 can be carried out by any suitable component within the imaging system 100 and all steps need not be carried out by the same component. In some embodiments, one or more steps of the method 1500 can be performed by, or at the direction of, a processor circuit of the imaging system 100, including, e.g., the processor 560 (FIG. 5) or any other component. The angiography-based data described with reference to FIG. 15 and the method 1500 may be any suitable form of data that is derived from or mapped to an x-ray angiography image. For example, such angiography-based data could include QCA data, angiography-based pressure ratio data (e.g., angio Pd/Pa, angio FFR, angio iFR, etc.), and angiography-based functional data (e.g., angio pressure and/or angio flow), or any other suitable data. For example, other data types include vascular perfusion data (e.g., myocardial perfusion imaging) with single photon emission computed tomography (SPECT) or positron emission tomography (PET).

Steps 1505 and 1510 may be substantially similar to steps 605 and 610 of the method 600 (FIG. 6). For example, at step 1505, the method 1500 includes receiving CT imaging data. The CT imaging data may be the same CT imaging data received at step 605 or may differ according to the patient anatomy imaged.

At step 1510, the method 1500 includes generating a 3D model 1905 (FIG. 19) of the patient's vasculature based on the CT imaging data. The CT-based three-dimensional model 1905 may be the same CT-based model 800 (FIG. 8) or may differ. The CT-based model 1905 may be generated based on CT imaging data corresponding to a different patient anatomy or different imaging procedure.

At step 1515, the method 1500 includes receiving an x-ray angiography image 1700 of the patient vasculature obtained at an imaging angle 1790. Step 1515 will be described with reference to FIG. 17, which is a diagrammatic view of an x-ray angiography image and an enlarged view of the x-ray angiography image with angiography-based data, according to aspects of the present disclosure. The angiography-based data may also be referred to as blood vessel metrics. In some embodiments, the angiography image 1700 may additionally be referred to as a roadmap, a roadmap image, a path, or any other suitable term.

The x-ray angiography image 1700 may be obtained via the x-ray imaging device 300 (FIG. 3) or the x-ray angiography imaging device 156 in conjunction with the x-ray angiography processing system 154 (FIG. 1) previously described or with any other similar device and processing system. The x-ray angiography image 1700 may correspond to an anatomy of any suitable region or structure of a patient anatomy including any of the previously mentioned parts of a patient anatomy. The patient anatomy imaged in the x-ray angiography image 1700 may be the same anatomy imaged in the fluoroscopy images used to create the CT-based 3D model 1905 at step 1510. A contrast agent may be introduced to the patient vasculature prior to obtaining the angiography image 1700. The x-ray angiography image 1700 may be acquired at any suitable angle 1790 with respect to the patient anatomy. This angle 1790 may be stored within a memory in communication with the system 100 and may be referred to as the imaging angle. As shown by the axes 1798 in FIG. 17, the x-ray angiography image 1700 is a two-dimensional image.

Figure 17:
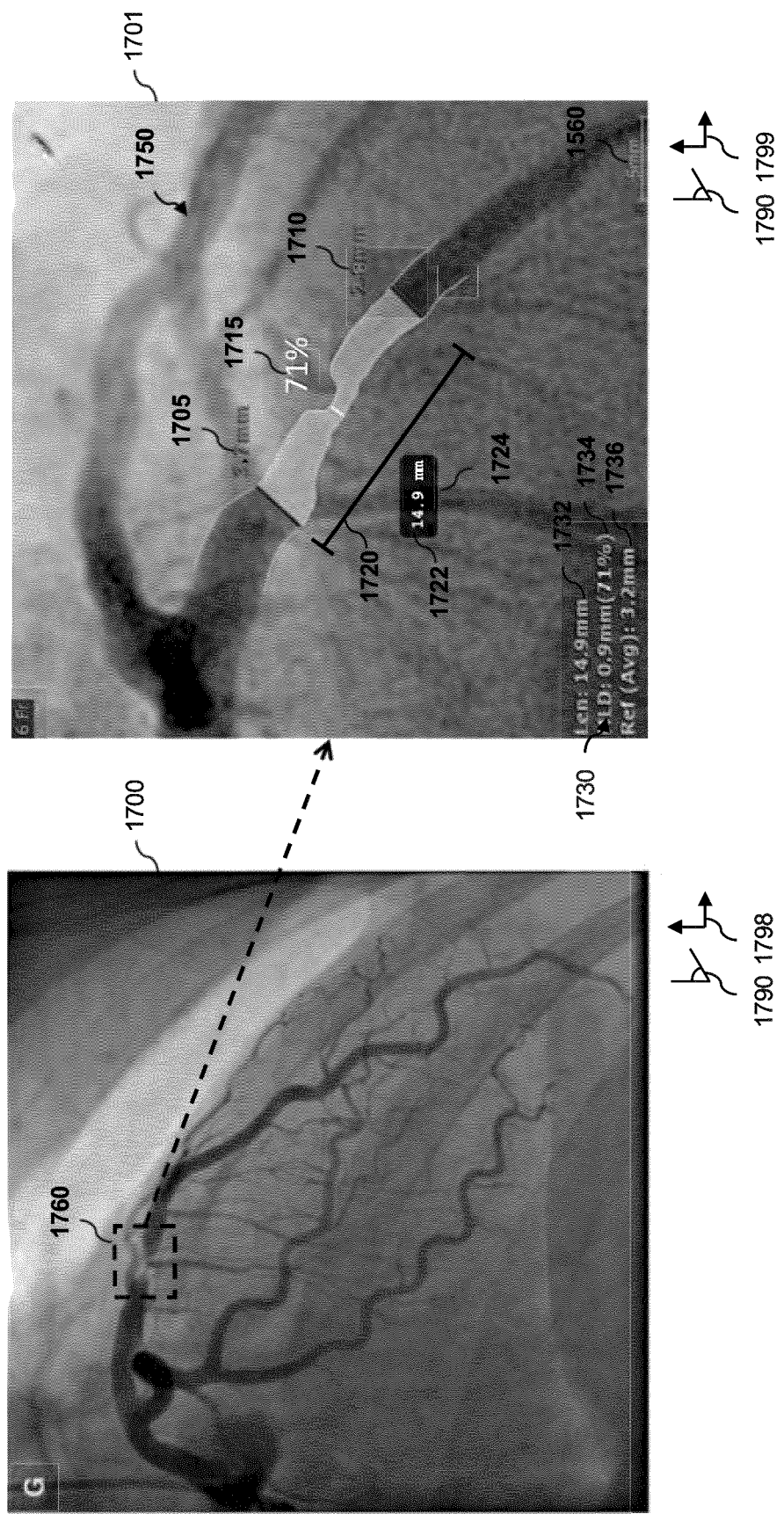
FIG. 17 is a diagrammatic view of an x-ray angiography image and an enlarged view of the x-ray angiography image with angiography-based data, according to aspects of the present disclosure.

At step 1520, the method 1500 includes determining blood vessel metrics 1750 based on the x-ray angiography image 1700. Step 1520 will also be described with reference to FIG. 17. FIG. 17 additionally depicts angiography-based data 1750 overlaid on an enlarged portion 1701 of the angiography image 1700. The enlarged portion 1701 of the image 1700 may be a portion of the angiography image 1700 as identified by the region 1760. The region 1760 may be any suitable portion of the angiography image 1700 and the region shown in FIG. 17 is merely exemplary. In some embodiments, the angiograph-based data or blood vessel metrics 1750 may be determined without selecting or identifying an enlarged portion 1701 of the image. The enlarged portion 1701 is shown in FIG. 17 to increase the visibility of various metrics discussed and may therefore be merely pedagogical in nature. As shown by the axes 1799, the enlarged portion 1701 of the angiography image 1700 is a two-dimensional image.

The angiography-based data 1750 within the enlarged portion 1701 of the angiography image 1700 includes lumen diameters 1705 and 1710, a minimum lumen diameter (MLD) value 1715, a length 1720, a length measurement 1722, a graphical element 1724, a scale 1760, and additional metrics 1730. The additional metrics 1730 include an additional length measurement 1732, MLD data 1734, and an average lumen diameter 1736. As previously mentioned, the angiography-based data 1750 may include any suitable angiography image-based data, including QCA data or any other suitable type of data.

In some embodiments, a user of the system 100 may select a region or length 1720 along an imaged vessel as shown in FIG. 17. In some embodiments, the system 100 may select the length 1720 automatically using any of the previously mentioned image processing or artificial intelligence techniques. In some embodiments, the length 1720 may include multiple vessels within the angiography image 1700 including any suitable landmark features previously described including bifurcations, occlusions, regions of tortuosity, lengths, or other landmark features.

Upon the selection of the length 1720, multiple angiography-based data 1750 may be determined. For example, at a proximal end of the selected length 1720, the lumen diameter 1705 may be determined. At a distal end of the selected length 1720, the lumen diameter 1710 may also be determined. The diameters 1705 and/or 1710 may additionally be referred to as reference diameters.

In some embodiments, the selected length 1720 of an imaged vessel may include an occlusion as shown in FIG. 17. The system 100 may identify the position of the occlusion and determine the MLD value 1715. The MLD value may correspond to the severity of the identified occlusion. The MLD value may be a percentage, as shown, or may additionally be a length measurement similar to the diameters 1705 and 1710 or may be any other type of metric to illustrate the severity of the occlusion. The MLD 1715 may be a percentage of occlusion. In some embodiments, a percentage value of MLD at the identified occlusion may be calculated based on the lumen diameter at the occlusion divided by an average of the diameters 1705 and 1710. In some embodiments, an MLD value 1715 may be calculated by the system 100 after any length 1720 is selected whether or not an occlusion is identified. The MLD value 1715 may assist a physician in determining the proper treatment of occlusions within the vasculature. For example, the MLD value 1715 may provide information relating to the type or size of stent to be placed within the patient vasculature.

The system 100 may also determine a length measurement 1722 of the selected length 1720. In an embodiment in which the angiography-based data 1750 is displayed to a user within the angiography image 1700 as shown in FIG. 17, the length measurement 1722 may be positioned within a graphical element 1724 near the length 1720 or an indicator of the length 1720. The length measurement 1722 may also be positioned elsewhere. The graphical element 1724 may be in any suitable position, however. For example, the graphical element 1724 may be positioned above, beneath, beside, or otherwise adjacent to the angiography image 1700. In addition, the graphical element 1724 may be of any suitable shape, type, color, opacity, or orientation. The graphical element 1724 may be or include any suitable symbol, graphical representation, or alpha-numeric characters. The graphical element 1724 may include any suitable metrics or angiograph-based data 1750 in addition to the length measurement 1722 shown.

The angiography-based data 1750 may additionally include the scale 1760. The scale 1760 may be positioned at any suitable location within the angiography image 1700 and may indicate to a user the scale of the image 1700. For example, the scale 1760 may display an exemplary length measurement in conjunction with a graphical element displaying how a structure of that exemplary length may appear within the angiography image 1700.

The angiograph-based data 1750 may also include any suitable additional metrics 1730. The length measurement 1732 may correlate to the length measurement 1722 previously described but may be included at a different location within the image 1700. In some embodiments, the length measurement 1732 may also correspond to a different length of the vasculature within the image 1700, such as the total length of vasculature shown, a previously selected length 1720, or any other suitable length.

The MLD data 1734 may include any information relating to an occlusion shown within the angiography image 1700 or along the selected length 1720 or any other location of minimum lumen diameter. The MLD data 1734 may include the MLD value 1715 previously discussed or may include additional values, percentages, or metrics. The MLD data 1734 may include a measured diameter of the lumen at a location of minimum diameter.

The average lumen diameter 1736 may also be included within the additional metrics 1730. The average lumen diameter 1736 may correspond to an average of the two lumen diameters 1705 and 1710 previously discussed. The average lumen diameter 1736 may also correspond to an average of all lumen diameters along the selected length 1720, may correspond to an average of all the diameters of lumens shown in the angiography image 1700, or may include some other statistical metric relating to the angiography-based data 1750 shown.

Any suitable additional metrics may be measured and determined in addition to or included with the angiography-based data 1750 described with reference to FIG. 17. The system 100 may also calculate other metrics based on the metrics shown, such as metrics related to blood pressure, blood flow, bifurcations, regions of tortuosity, vessel trauma, scarring, or any other suitable metrics. In some embodiments, any or all of the previously mentioned metrics may be calculated without a user or the system 100 selecting a region of length 1720. Any of the mentioned angiography-based data 1750 may be determined for vessels observed within the image as a whole or in part. In some embodiments, the metrics discussed may be calculated, but not displayed to a user. In addition, the angiography image 1700 may not be displayed to a user. Rather, the angiography-based data 1750 may be calculated by the system 100 and stored within a memory. The angiography-based data 1750 may also be displayed to a user overlaid on or in conjunction with images or models different from the angiography image 1700.

Any or all of the previously mentioned angiography-based data 1750 may be calculated through any suitable method. For example, the data may be determined via image processing or artificial intelligence techniques. The data may be determined using edge detection techniques to identify the locations and borders of vessels within the angiography image 1700. The system 100 may additionally use any suitable optimization, calibration, or validation methods to identify features or structures of interest within the angiography image 1700.

At step 1525, the method 1500 includes generating multiple CT-based 2D pathways 1820 by projecting a CT-based 3D model 1810 at angles similar to the imaging angle. Step 1525 will be described with reference to FIG. 18, which is a diagrammatic view illustrating a relationship between the x-ray angiography image 1700, angiography-based data 1750, a CT-based 2D pathway 1820, and a CT-based 3D model 1810, according to aspects of the present disclosure. The step 1525 may be similar to, or share features or characteristics with, the step 625 of the method 600 described with reference to FIG. 6.

Figure 19:
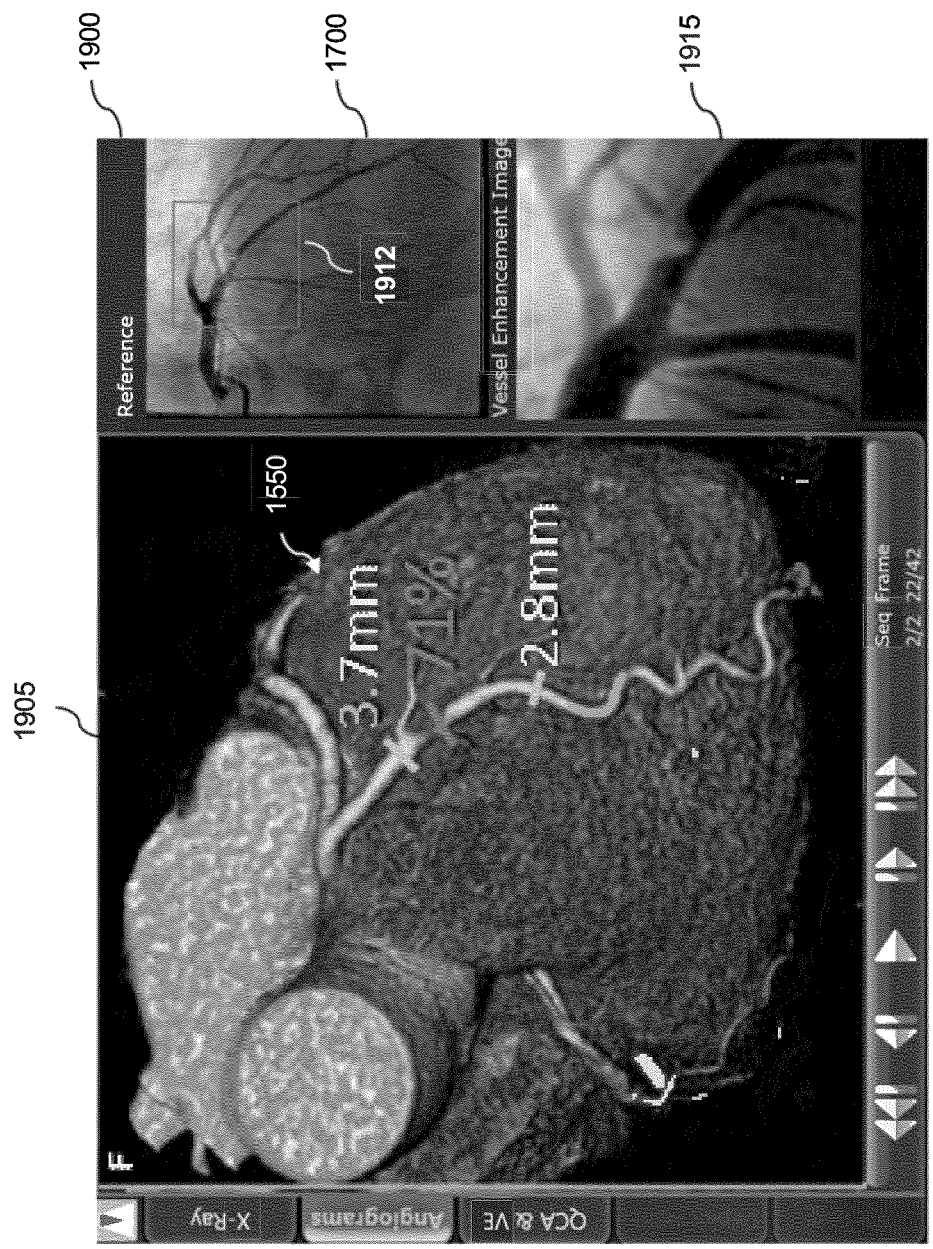
FIG. 19 is a diagrammatic view of a graphical user interface displaying angiography-based data co-registered to a CT-based 3D model, according to aspects of the present disclosure.

Similar to the step 625 of the method 600, at step 1525, the system 100 may extract a model 1810 of the vascular tree from the CT model 1905 of FIG. 19. The 3D CT model 1905 of FIG. 19 shows the vessels within and around the heart imaged as well as various other tissues, cavities, or other structures within and/or around the heart. The system 100 may use the model 1905 to construct a new model 1810 representing only the vessels of the heart. The CT-based 3D model 1810 may be a three-dimensional model as shown by the axes 1899. Constructing a new 3D model 1810 based on the 3D model 1905 to include only the vessels of the heart may be accomplished by a similar method as was used by the system 100 at step 625 of the method 600 to construct the CT-based 3D model 910 (FIG. 9) from the model 800 (FIG. 8).

The CT-model 1810 may be projected from three-dimensional space to two-dimensional space to create a CT-based 2D pathway 1820 at an angle 1891. The angle 1891 may be referred to as the projection angle. The angle 1891 may be any suitable angle. In some embodiments, the angle 1891 may be the same as the imaging angle 1890 or the angle at which the x-ray angiography image 1700 was obtained. In some embodiments, the angle 1891 may differ from the angle 1890 by one or more degrees. As shown by the axes 1898, the CT-based pathway 1820 is a two-dimensional image or model.

Any suitable method may be used by the system 100 to project the CT-based 3D model 1810 to create the CT-based 2D pathway 1820 including any of the methods, processes, or techniques including the matrix transformations and projection techniques described with reference to projecting the CT-based 3D model 910 to the CT-based 2D model 920 with reference to FIG. 9 and step 625 of the method 600.

At step 1525 the method 1500 also includes creating multiple CT-based 2D pathways 1820. Similar to the CT-based pathways 920 previously described, these multiple CT-based pathways 1820 may be created by varying the angle of projection 1891 for each pathway 1820. The two-dimensional pathways 1820 may vary due to a difference in perspective between each pathway 1820. The projection angles 1891 used to create the multiple CT-based 2D pathways 1820 may each vary by standard increments similar to the angles 990 described with reference to FIG. 9 and the set of CT-based 2D pathways 1820 may include any suitable number. The projection angles 1891 may be similar to the imaging angle 1890 or may differ. The creation of the pathways 1820 at step 1525 may share any suitable characteristics of the step 625 of the method 600 described previously.

At step 1530, the method 1500 includes identifying a CT-based pathway 1820 that is similar to the x-ray angiography image 1700. The step 1530 may be substantially similar to the step 630 of the method 600 and the system 100 may use any of the methods or processes described previously in relation to the step 630 to perform the step 1530. Specifically, each generated pathway 1820 may be compared to the angiography image 1700. In some embodiments, the system 100 may identify a set of two-dimensional coordinates corresponding to the vessels shown in the angiography image 1700. This collection or set of two-dimensional coordinates may be a two-dimensional pathway or path similar to the fluoroscopy-based 2D pathway 1040 previously discussed. This two-dimensional pathway may be compared with the CT-based 2D pathways 1820 in the same way as the fluoroscopy-based pathway 1040 was compared to the CT-based pathways 920 described previously. In other embodiments, the system 100 may compare the CT-based pathways 1820 to the angiography image 1700 itself. The system 100 may use any appropriate method, algorithm, or process to compare the CT-based 2D pathways 1820 with the angiography image 1700 including any of the methods, algorithms, or processes described with reference to FIGS. 11 and 12. At the step 1530, the system 100 may identify a CT-based 2D pathway 1820 which is sufficiently similar to the vessels of the angiography image 1700.

At step 1535, the method 1500 includes co-registering the blood vessel metrics 1750 and the identified CT-based 2D pathway 1820 by mapping locations of the angiography image 1700 and the CT-based 2D pathway. Step 1535 will be described with reference to FIG. 18. Step 1535 may be substantially similar to the step 635 of the method 600 and may include any of the same description of the step 635 previously discussed.

At step 1535, the system 100 may associate anatomical features identified in the angiography image 1700 with the same anatomical features in the identified CT-based 2D pathway 1820 to create a mapping. The anatomical features identified may be any suitable features including those listed with reference to step 635 of the method 600. This association of anatomical features in the angiography image 1700 and the CT-based 2D pathway 1820 creates a mapping of physical positions or locations along the vasculature shown in the image 1700 and pathway 1820. The system 100 identifies the previously listed anatomical landmarks, the system 100 may identify anatomical landmarks via any suitable method including any previously described with reference to the step 635 of the method 600. The feature mapping of locations within the vessel defined by the angiography image 1700 and the CT-based 2D pathway 1820 may be expanded to include a one-to-one mapping of all locations along the vessels including locations at anatomical landmarks or not at anatomical landmarks. This mapping may be created with any suitable method including those listed with reference to step 635 of the method 600.

After a mapping between corresponding locations along the vessels of the angiography image 1700 and the CT-based 2D pathway 1820 has been established, the blood vessel metrics or angiography-based data 1750 may be co-registered to the CT-based 2D pathway 1820. This co-registration may be represented both by the arrow 1864 and the arrow 1865 shown in FIG. 18. Specifically, the angiography-based data 1750 may be associated with the CT-based 2D pathway 1820 as shown by the arrow 1865 and the location data corresponding to the angiography-based data 1750 may be associated with the pathway 1820 as shown by the arrow 1864. The relationship between the angiography-based data 1750 and its location within the angiography image 1700 may be illustrated by the arrow 1861.

At step 1540, the method 1500 includes co-registering the blood vessel metrics 1750 and the CT-based 3D model 1810 based on the mapping created at step 1535. The step 1540 will also be described with reference to FIG. 18. The step 1540 may be substantially similar to the step 640 of the method 600 and may include any of the same description of the step 640 previously discussed.

To co-register the angiography-based data 1750 to the CT-based 3D model 1810, the CT-based 2D pathway 1820 may be projected back to the CT-based 3D model 1810 such that all the angiography-based data 1750 or any other suitable data co-registered to the CT-based 2D pathway 1820 may be similarly co-registered to the CT-based 3D model 1810. For example, the location information corresponding to any received data may be received, or a correspondence between the same locations may be established, as shown by the arrow 1867. Similarly, the angiography-based data 1750 or any other data may be co-registered with the CT-based 3D model 1810 as shown by the arrow 1866. This projection of the CT-based 2D pathway 1820 may be performed by calculating an inverse of the transformation matrices and/or equations used to create the 2D pathway 1820. The equations and/or techniques used may include the projection angle 1891 and may include any of the methods, techniques, or processes described with reference to the step 640 of the method 600. As shown by the axes 1899, the CT-based model 1810 is three-dimensional. As shown by the axes 1897, the angiography image 1700 and the enlarged view 1701 of the angiography image 1700 shown in FIG. 18 are two-dimensional images.

At step 1545, the method 1500 includes outputting to a display a CT-based 3D model 1905 and graphical representations of the blood vessel metrics 1750. Step 1550 will be described with reference to FIGS. 19 and 20. FIG. 19 is a diagrammatic view of a graphical user interface 1900 displaying angiography-based data 1750 co-registered to a CT-based 3D model 1905, according to aspects of the present disclosure. FIG. 19 additionally depicts the angiography image 1700, an enlarged view 1915 of the angiography image 1700, and an indicator 1912.

Figure 18:
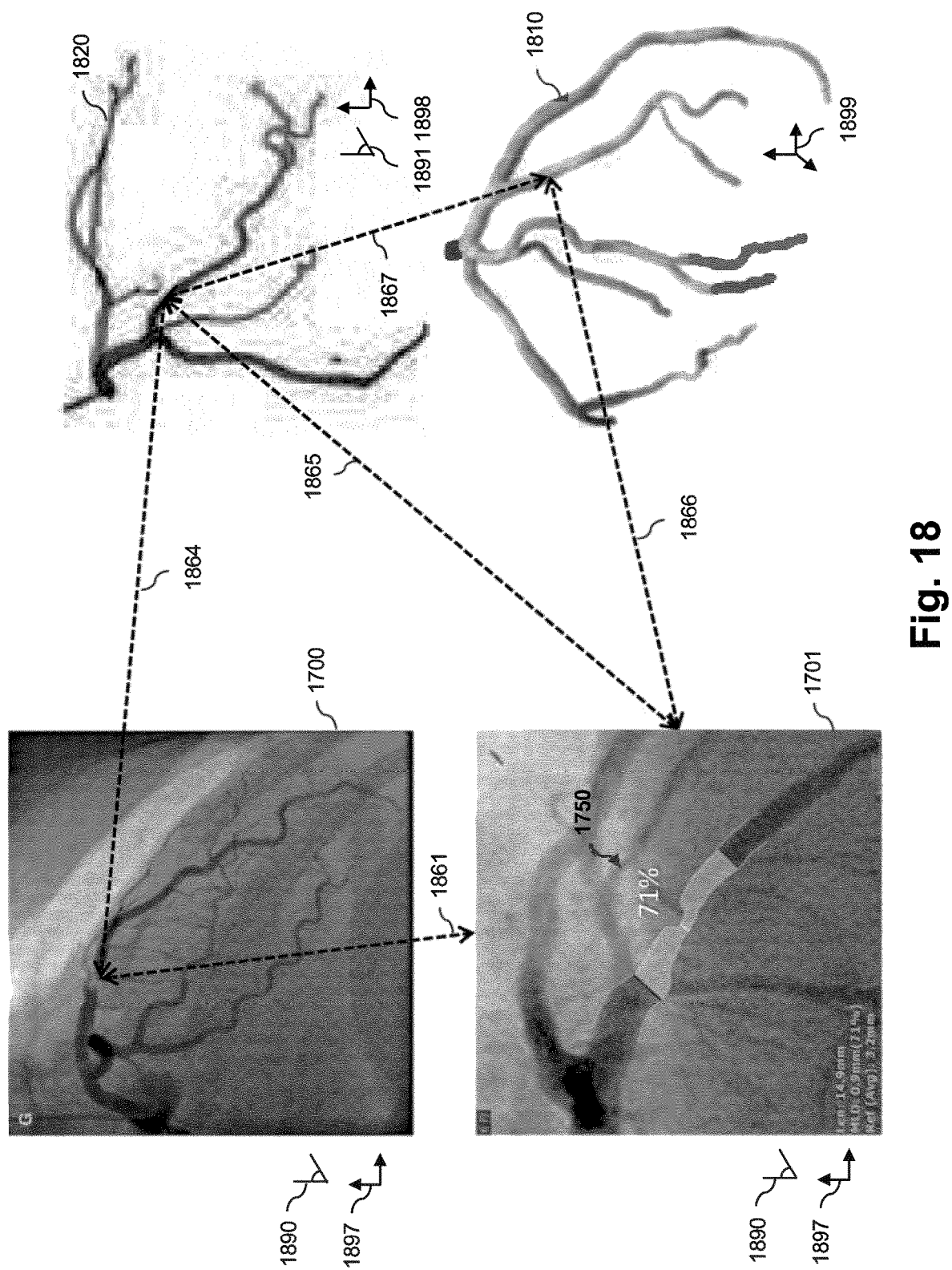
FIG. 18 is a diagrammatic view of a relationship between an x-ray angiography image, angiography-based data, a CT-based 2D pathway, and a CT-based 3D model, according to aspects of the present disclosure.

The CT-based model 1905 output to a display may be either the CT-based 3D model 1810 shown in FIG. 18 or may be a CT-based 3D model similar to the CT-based model 800 shown in FIG. 8. In some embodiments, the CT-based model 1905 may be the CT-based model from which the vasculature tree model 1810 was extracted at step 1510. The CT-based model 1905 with co-registered angiography-based data 1750 may be displayed to a user in any suitable format. For example, as shown in FIG. 19, the angiography-based data 1750 may be displayed overlaid on the CT-based model 1905. The angiography-based data 1750 may be QCA data. In other embodiments, co-registered angiography-based data 1750 may include any other suitable images, metrics, or other data. The co-registered angiography-based data 1750 may also be positioned beside the CT-based model 1905 or arranged or displayed in any other suitable configuration.

In the embodiment shown in FIG. 19, the angiography-based data 1750 determined at step 1520 and shown in FIG. 17 in more detail is positioned overlaid on the CT-based model 1905. As shown, the amount, type, or form of display of the data 1750 may differ from FIG. 17. In some embodiments, a user of the system 100 may specify which data 1750 to view on the graphical user interface 1900. In some embodiments, all angiography-based data 1750 displayed in FIG. 16 may also be included within the graphical user interface 1900 shown in FIG. 19.

Adjacent to the CT-based model 1905, the angiography image 1700 is shown. In some embodiments, the angiography image 1700 may be replaced with any other suitable angiography image. In some embodiments, a physician may obtain additional angiography images during an x-ray angiography procedure. Any of these images may be displayed adjacent to, or otherwise in conjunction with the CT-based model 1905. The angiography image 1700 may correspond to a view or angle of the CT-based model 1905 as displayed to the user or may differ. In some embodiments, the system 100 may additionally display an enlarged portion 1915 of the angiography image 1700. The enlarged portion 1915 of the angiography image 1700 may assist a user to observe landmark features or other features of interest within the angiography image 1700. The indicator 1912 may convey to a user the section of the angiography image 1700 corresponding to the enlarged portion 1915. In some embodiments, a user of the system 100 may select the section of the angiography image 1910 to be displayed by creating the indicator 1912 within the image 1700 with any suitable command input device, such as a computer mouse, keyboard, touchscreen, or any other suitable device. In some embodiments, the graphical user interface 1900 may additionally or alternatively include an enlarged view of the CT-based model 1905. In some embodiments, the metrics 1750 may additionally be displayed on the angiography image 1700, the enlarged portion 1915 of the angiography image 1700, or the enlarged portion of the CT-based model 1905.

Figure 20:
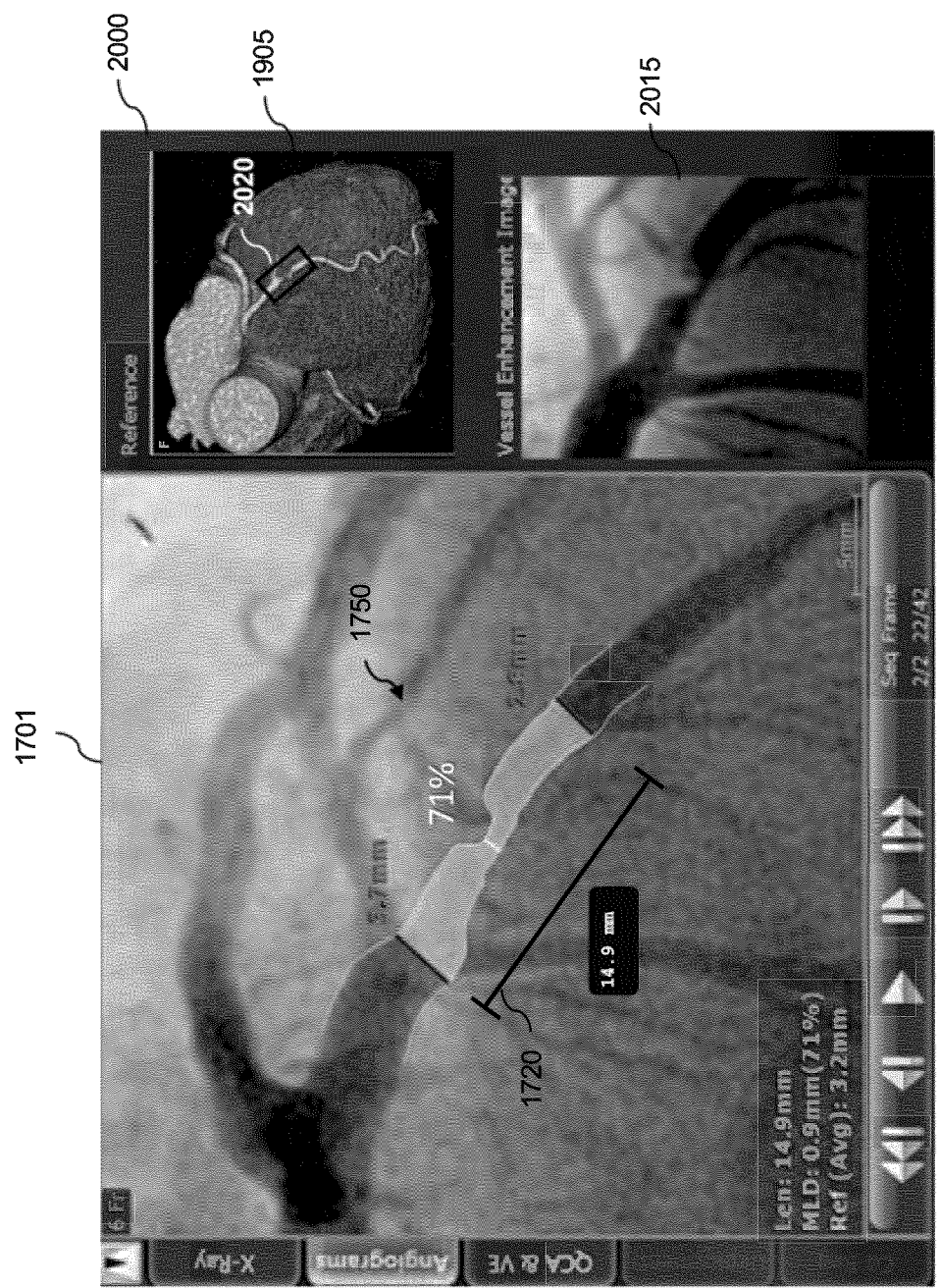
FIG. 20 is a diagrammatic view of a graphical user interface displaying angiography-based data co-registered to a CT-based 3D model, according to aspects of the present disclosure.

FIG. 20 is a diagrammatic view of a graphical user interface 2000 displaying angiography-based data 1750 co-registered to the CT-based 3D model 1905, according to aspects of the present disclosure. FIG. 20 includes the angiography image 1700, angiography-based data 1750, the CT-based model 1905, a region 2020, and an enlarged portion 2015 of the angiography image 1700.

An additional exemplary graphical user interface 2000 may display the angiograph-based data 1750 overlaid on the original angiography image 1700 used to calculate the angiography-based data 1750 at step 1520. In other embodiments, the angiography image 1700 may be a different angiography image including any previously listed. In some embodiments, a user of the system 100 may select any angiography image to be displayed within the graphical user interface 2000 and the system 100 may overlay the angiography-based data 1750 on the selected angiography image. The angiography data 1750 may be arranged on or beside the angiography image 1700 in any suitable configuration or arrangement and may be of any suitable form or type as described with reference to FIG. 17.

The CT-based model 1905 may be displayed in conjunction with the angiography image 1700. For example, as shown in FIG. 20, it may be positioned adjacent to the angiography image 1700. In some embodiments, the angiography-based data 1750 may additionally be overlaid on the CT-based model 1905. In other embodiments, the region 2020 may be overlaid over the CT-based model 1905. The region 2020 may indicate the location within the CT-based model 1905 of the selected length 1720 discussed with reference to FIG. 17. In some embodiments, the region 2020 may instead correlate to the region shown by the angiography image 1700 as a whole within the CT-based model 1905.

The system 100 may additionally display an enlarged portion 2015 of the angiography image 1700. The enlarged portion 2015 of the angiography image 1700 may assist a user to observe landmark features or other features of interest within the angiography image 1700 in more detail. In some embodiments, an indicator may be included within the angiography image 1700 to convey to a user the section of the angiography image 1700 corresponding to the enlarged portion 2015. In some embodiments, a user of the system 100 may select the section of the angiography image 1700 to be displayed by creating the indicator within the image 1700. In some embodiments, the graphical user interface 2000 may additionally or alternatively include an enlarged view of the CT-based model 1905. In some embodiments, the metrics 1750 may additionally be displayed on the enlarged portion 2015 of the angiography image 1700, or the enlarged portion of the CT-based model 1905.

It is understood that the data, metrics, features, graphical elements, graphical representations, images, or any other aspects of the graphical user interfaces 1900 (FIG. 19) and/or 2000 are merely exemplary and any other additional data, metrics, features, graphical elements, graphical representations, images, or any other aspects are fully contemplated. In addition, the arrangement of the elements listed above is also exemplary. Any suitable configuration, arrangement, or organization is also fully contemplated.

Figure 16:
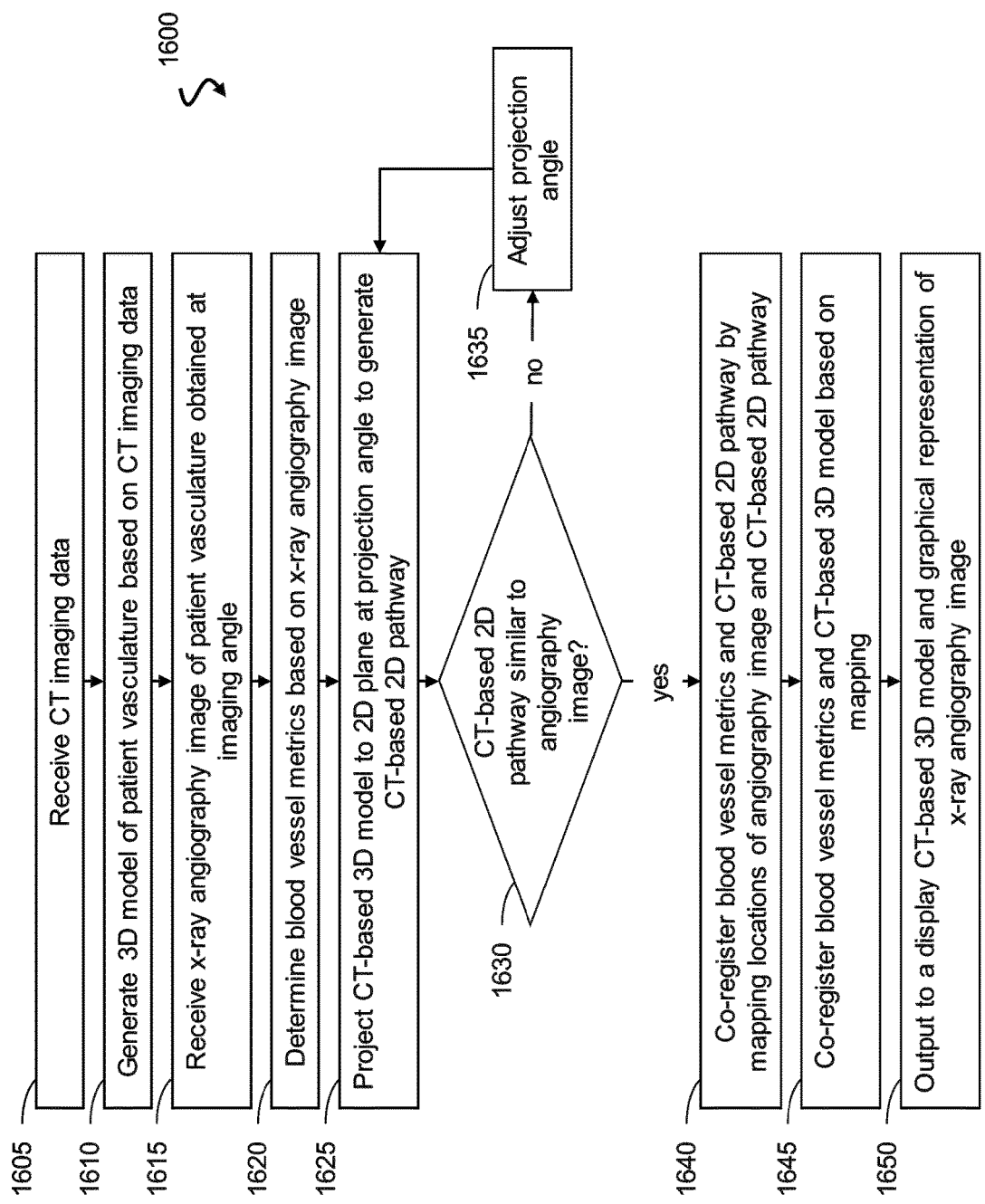
FIG. 16 is a flow diagram of a method of co-registering angiography-based data with a CT-based 3D model, according to aspects of the present disclosure.

FIG. 16 is a flow diagram of a method of co-registering angiography-based data with a CT-based 3D model, according to aspects of the present disclosure. As illustrated, the method 1600 includes a number of enumerated steps, but embodiments of the method 1600 may include additional steps before, after, or in between the enumerated steps. In some embodiments, one or more of the enumerated steps may be omitted, performed in a different order, or performed concurrently. The steps of the method 1600 can be carried out by any suitable component within the diagnostic system 100 and all steps need not be carried out by the same component. In some embodiments, one or more steps of the method 1600 can be performed by, or at the direction of, a processor circuit of the diagnostic system 100, including, e.g., the processor 560 (FIG. 5) or any other component.

The method 1600 is an additional embodiment of the present disclosure. Various steps of the method 1600 may be substantially similar to steps of the method 1500 previously described. Specifically, the steps 1605-1620 of the method 1600 are the same as the steps 1505-1520 of the method 1500.

Steps 1625, 1630, and 1635 of the method 1600 may be substantially similar to the steps 725, 730, and 735 of the method 700. Specifically, step 1625 of the method 1600 includes projecting the CT-based 3D model 1810 to a 2D plane at a projection angle 1891 to generate a CT-based 2D pathway 1820. The model 1810 may be projected to a 2D plane at the projection angle 1891 using any of the previously mentioned transformation matrices or may involve any of the previously mentioned image processing or machine learning techniques as the step 725 of the method 700. Only one CT-based 2D pathway 1820 is created at the step 1625. Similar to the steps 725, 730, and 735, the system may incrementally adjust the projection angle 1891 after comparing each CT-based 2D pathway 1820 if the differences between the CT-based 2D pathway 1820 and the vessels of the angiography image 1700 are within a predetermined threshold. One difference between the step 1630 and the step 730 is that the CT-based 2D pathways 1820 are compared to the angiography image 1700 rather than the fluoroscopy-based 2D pathway 1040 of FIG. 10. However, the steps 1625, 1630, and 1635 may include any of the description of the steps 720, 730, and 735 previously described with reference to the method 700 of FIG. 7.

A shown in FIG. 16, the steps 1640-1650 of the method 1600 are the same as the steps 1535-1545 of the method 1500. Therefore, no specific description will be given with reference to steps 1640-1650 because the description of steps 1640-1650 is the same as the description of the steps 1535-1545.

It is noted that the procedures described herein, including obtaining CT data to generate a CT-based model 800 (FIG. 8), obtaining intravascular data 1030 and fluoroscopy images 1010 (FIG. 10), or obtaining angiography image 1700 (FIG. 17) may be performed at various times in relation to one another. In some embodiments, each procedure may be performed concurrently such that one procedure is completed immediately following another. In other embodiments, more time may pass between each procedure. The amount of time between each procedure may be limited to prevent significant change to the patient anatomy between each procedure. Such change may be a result of natural growth, trauma, healing, therapy, or any other event or process which may alter the patient anatomy between procedures.

One or more fluoroscopy-based or angiography-based 2D pathway(s) and one or more CT-based 2D pathway(s) can be representative of the same vessel and/or the same portion of the same vessel. In that sense, the fluoroscopy-based or angiography-based 2D pathways and CT-based 2D pathways can be considered the same and/or representative of the same location of the patient body. Thus, fluoroscopy-based or angiography-based 2D pathways and CT-based 2D pathways can be the same shape or similar shape. The fluoroscopy-based or angiography-based 2D pathways and CT-based 2D pathways can be determined in different ways. In that sense, the fluoroscopy-based or angiography-based 2D pathways and CT-based 2D pathways can be considered different views or different forms of the same pathway, same vessel, and/or same location of the patient body. The fluoroscopy-based 2D pathways can be generated by tracking the position of the intravascular device in the x-ray fluoroscopy images (e.g., the shape traced out by movement of the intravascular device). The angiography-based 2D pathways can be the shape occupied by contrast agent within the vessel. The CT-based 2D pathways can be generated by projecting the CT-based 3D model at different angles.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A co-registration system, comprising:
a processor circuit configured for communication with a display, an x-ray fluoroscopy device, and an intravascular catheter or guidewire, wherein the processor circuit is configured to:
receive, from the x-ray fluoroscopy device, a plurality of x-ray fluoroscopy images of the blood vessel while the intravascular catheter or guidewire moves through the blood vessel;
receive, from the intravascular catheter or guidewire, intravascular data representative of the blood vessel while the intravascular catheter or guidewire moves through the blood vessel;
generate, using the plurality of x-ray fluoroscopy images, a first two-dimensional (2D) pathway of the blood vessel based on the intravascular catheter or guidewire moving through the blood vessel;
generate a second 2D pathway of the blood vessel using a three-dimensional (3D) model of the blood vessel based on computed tomography (CT) imaging data;
perform a first co-registration between the intravascular data and the second 2D pathway based on a mapping between corresponding locations of the first 2D pathway and the second 2D pathway;
perform a second co-registration between the intravascular data and the 3D model based on the first co-registration; and
output, to the display, the 3D model and a graphical representation of the intravascular data at a co-registered location of the 3D model.

2. The system of claim 1, wherein the processor circuit is configured to:
determine if the first 2D pathway and the second 2D pathway are comparable; and
perform the first co-registration only in response to determining that the first 2D pathway and the second 2D pathway are comparable.

3. The system of claim 2, wherein the processor circuit is configured to:
compute a similarity measure representative of if the first 2D pathway and the second 2D pathway are comparable;
determine that the first 2D pathway and the second 2D pathway are comparable when the similarity measure satisfies a threshold.

4. The system of claim 2, wherein the processor circuit is configured to:
generate a plurality of 2D pathways of the blood vessel using the 3D model of the blood vessel based on CT imaging data; and
select a given 2D pathway of the plurality of 2D pathways as the second 2D pathway when the given 2D pathway and the first 2D pathway are comparable.

5. The system of claim 4, wherein the plurality of 2D pathways correspond to a plurality of angles for projecting the 3D model to a 2D plane.

6. The system of claim 1, wherein the processor circuit is configured to use an angle at which the plurality of x-ray fluoroscopy images were obtained to generate the second 2D pathway.

7. The system of claim 1, wherein the processor circuit is configured to compute a first projection of the 3D model to a 2D plane to generate the second 2D pathway.

8. The system of claim 7, wherein the processor circuit is configured to compute a second projection from the second 2D pathway to the 3D model to perform the second co-registration, wherein second projection is an inverse of the first projection.

9. The system of claim 1, wherein the intravascular data comprises at least one of pressure data, flow data, or imaging data.

10. The system of claim 1, wherein the first 2D pathway and the second 2D pathway are representative of a same portion of the blood vessel.

* * * * *